(12) United States Patent
Kasuto et al.

(10) Patent No.: US 10,851,341 B2
(45) Date of Patent: *Dec. 1, 2020

(54) METHODS AND SYSTEMS FOR HARVESTING CELLS

(71) Applicant: PLURISTEM LTD., Haifa (IL)

(72) Inventors: Harel Kasuto, Kibbuts Yifat (IL); Nirit Drori-carmi, Kibbutz Nahsholim (IL); Barak Zohar, Karmiel (IL)

(73) Assignee: Pluristem Ltd., Haifa (IL)

( * ) Notice: Subject to any disclaimer, the term of this patent is extended or adjusted under 35 U.S.C. 154(b) by 46 days.

This patent is subject to a terminal disclaimer.

(21) Appl. No.: 15/594,999

(22) Filed: May 15, 2017

(65) Prior Publication Data
US 2017/0247656 A1 Aug. 31, 2017

Related U.S. Application Data

(63) Continuation of application No. 14/009,952, filed as application No. PCT/IB2012/000933 on Apr. 15, 2012, now Pat. No. 9,657,266.
(Continued)

(51) Int. Cl.
*C12M 1/12* (2006.01)
*C12N 5/073* (2010.01)
(Continued)

(52) U.S. Cl.
CPC ........... *C12N 5/0605* (2013.01); *C12M 25/14* (2013.01); *C12M 25/18* (2013.01); *C12M 33/08* (2013.01); *C12M 47/02* (2013.01); *C12N 5/0075* (2013.01); *C12N 5/0602* (2013.01); *C12N 5/0668* (2013.01); *C12N 2527/00* (2013.01); *C12N 2533/30* (2013.01)

(58) Field of Classification Search
None
See application file for complete search history.

(56) References Cited

U.S. PATENT DOCUMENTS 4,664,912 A 5/1987 Wiktor et al.
6,911,201 B1 6/2005 Merchav et al.
(Continued)

FOREIGN PATENT DOCUMENTS

EP 1284285 A2 2/2003
JP H04-126068 4/1992
(Continued)

OTHER PUBLICATIONS

"R. E. Spier and J. P. Whiteside, The Production of Foot-and-Mouth Disease Virus from BHK 21 C 13 Cells Grown on the Surface of Glass Spheres, 1976, Biotechnology and Bioengineering, vol. XVIII, pp. 649-657".
(Continued)

*Primary Examiner* — Renee Claytor
*Assistant Examiner* — Trent R Clarke

(57) ABSTRACT

Methods for using vibration to harvest cells grown in 3D culture are provided. The methods entail the application of force cells attached to a 3D matrix of sufficient amplitude, frequency, and duration to detach cells from the matrix and to flush the detached cells out of the matrix material. An apparatus for performing the methods of the invention as provided.

20 Claims, 15 Drawing Sheets

Related U.S. Application Data

(60) Provisional application No. 61/475,761, filed on Apr. 15, 2011.

(51) Int. Cl.
  *C12N 5/00* (2006.01)
  *C12N 5/0775* (2010.01)
  *C12M 1/26* (2006.01)
  *C12M 1/00* (2006.01)
  *C12N 5/071* (2010.01)

(56) References Cited

U.S. PATENT DOCUMENTS

| | | |
|---|---|---|
| 7,534,609 B2 | 5/2009 | Merchav et al. |
| 7,678,573 B2 | 3/2010 | Merchav et al. |
| 8,394,631 B2 | 3/2013 | Hampson et al. |
| 8,524,496 B2 | 9/2013 | Meiron et al. |
| 8,529,888 B2 | 9/2013 | Meiron et al. |
| 9,096,827 B2 | 8/2015 | Meiron et al. |
| 9,393,273 B2 | 7/2016 | Meiron |
| 9,512,393 B2 | 12/2016 | Kasuto et al. |
| 2005/0176143 A1 | 8/2005 | Merchav et al. |
| 2005/0181504 A1 | 8/2005 | Merchav et al. |
| 2007/0013963 A1 | 1/2007 | Nakamura |
| 2007/0163963 A1 | 7/2007 | Faustman et al. |
| 2009/0004738 A1 | 1/2009 | Merchav et al. |
| 2010/0209403 A1 | 8/2010 | Meiron et al. |
| 2011/0129447 A1 | 6/2011 | Meretzki et al. |
| 2011/0129486 A1 | 6/2011 | Meiron |
| 2011/0171182 A1 | 7/2011 | Abelman |
| 2011/0256108 A1 | 10/2011 | Meiron et al. |
| 2011/0256159 A1 | 10/2011 | Meiron et al. |
| 2011/0256160 A1 | 10/2011 | Meiron et al. |
| 2011/0293583 A1 | 12/2011 | Aberman |
| 2012/0122220 A1 | 5/2012 | Merchav et al. |
| 2013/0004465 A1 | 1/2013 | Aberman |
| 2013/0039892 A1 | 2/2013 | Aberman |
| 2013/0259843 A1 | 10/2013 | Duda et al. |
| 2013/0323213 A1 | 12/2013 | Meiron et al. |
| 2013/0337558 A1 | 12/2013 | Meiron et al. |
| 2014/0017209 A1 | 1/2014 | Aberman et al. |
| 2014/0242039 A1 | 8/2014 | Meiron et al. |
| 2015/0125138 A1 | 5/2015 | Kamieli et al. |
| 2015/0216907 A1 | 8/2015 | Chajut et al. |
| 2015/0232797 A1 | 8/2015 | Kasuto et al. |
| 2016/0022738 A1 | 1/2016 | Meretski et al. |
| 2016/0058799 A1 | 3/2016 | Aberman |
| 2016/0186259 A1 | 6/2016 | Ofir et al. |
| 2016/0271184 A1 | 9/2016 | Meiron |

FOREIGN PATENT DOCUMENTS

| | | | |
|---|---|---|---|
| WO | 2007/108003 A2 | 9/2007 | |
| WO | WO-2009037690 A1 * | 3/2009 | ............. A61K 35/28 |

OTHER PUBLICATIONS

Leonard Weiss, Tumor Necrosis and Cell Detachment, 1977, Int. J. Cancer, vol. 20, pp. 87-92.

"Sven H. Behrens and David G. Grier, The charge of glass and silica surfaces, 2001, The Journal of Chemical Physics vol. 115, pp. 6716-6721".

"NPL pdf 'Variomag product brochure online Apr. 10, 2008' downloaded from http://www.labobaza.pl/download/productFile/9040shake_thermo.pdf accessed May 28, 2015".

International Search Report Publication dated Jan. 11, 2013 from the International Searching Authority Re.: Application No. PCT/IB2012/000933.

Spier et al., 'Trypsinization of BHK-21 Mono Layer Cells Grown in 2 Large-scale Unit Process Systems' Biotechnology and Bioengineering, 19: 1735-38, Nov. 1977.

Chaproniere et ai, "Serial Culture of Single Adult Human Prostatic Epithelial Cells in Serum-free Medium Containing Low Calcium and a New Growth Factor from Bovine Brain,", Cancer Research, 46: 819-24, Feb. 1986.

"Sun et al. ""A Cell-detaching Reactor for Inoculation of Anchorage-dependent CHD and Vero Cells Between Stepwise-expanded Bioreactors""", Bbiotechnology Letters, 29; 697-701, May 2007."

"R. E. Spier and J. P. Whiteside, The Scale-Up from 0.1 to 100 Liter of a Unit Process System Based on 3-mm-Diameter Glass Spheres for the Production of Four Strains of FMDV from BHK Monolayer Cells, 1981, Biotechnology and Bioengineering, vol. XXIII, pp. 551-565".

"R. E. Spier and J. P. Whiteside, The Production of Foot-and-Mouth Disease Virus from BHK 21 C 13 Cells Grown on the Surface of DEAE Sephadex A50 Beads, 1976, Biotechnology and Bioengineering, vol. XVIII, pp. 659-667".

* cited by examiner

METHODS AND SYSTEMS FOR HARVESTING CELLS

CROSS-REFERENCE TO RELATED APPLICATIONS

This application is a Divisional of Ser. No. 14/009,952, filed Oct. 4, 2013, which is the National Stage of PCT/IB2012/000933, filed Apr. 15, 2012, which claims benefit of U.S. Provisional Application No. 61/475,761, filed Apr. 15, 2011, the disclosure of which is incorporated herein by reference in its entirety.

FIELD OF THE INVENTION

The present invention relates to methods and systems for harvesting cells grown in culture. More particularly, the invention relates to methods and systems for harvesting cells grown in vitro on a three-dimensional ("3D") substrate by applying a vibratory force of sufficient frequency, amplitude, and duration to release the cells from the 3D matrix so they may be recovered with high yield, and high cell viability and vitality. The vibratory force may also be used to seed cells onto the matrix prior to growth and also to effectively mix media through the 3D matrix during growth of the cells in a 3D bioreactor system.

Populations of cells, such as mammalian or human cells, are becoming increasingly important in medicine as biologic agents useful for treating a variety of different medical conditions. For example, there has been considerable interest focused on the therapeutic potential of human cells for various medical applications including tissue repair of damaged organs such as the brain, heart, bone and liver, and to support bone marrow transplantation (BMT). One class of human cells, adult stem cells, have been evaluated for treating and curing various conditions such as hematopoietic disorders, heart disease, Parkinson's disease, Alzheimer's disease, stroke, burns, muscular dystrophy, autoimmune disorders, diabetes, and arthritis.

Another class of human cells of interest are adherent stromal cells ("ASCs"). ASCs are heterogeneous populations of cells that may be obtained from bone marrow, adipose tissue, placenta, or blood. ASCs and their use in propagating hematopoietic stem cells in vitro are described in U.S. Pat. No. 6,911,201, which is incorporated by reference in its entirety.

Because of their diverse medical uses for both clinical and research purposes, there is a growing need for ASCs in large quantities. Obstacles to using these cells lie in the technical difficulty of isolating large quantities of normally occurring populations of adherent stromal cells due to the limited quantity of these cells in most tissues, and the discomfort and risk involved in the procedures for obtaining ASCs.

One solution to the problem of limited numbers of ASCs is to culture the cells in vitro in a 3D culture system under conditions that permit expansion of the cells. WO 2007/108003, which is incorporated by reference herein in its entirety, discloses methods for expansion of ASCs by culture in a 3D bioreactor, and use of the cells in therapy. Expansion of ASCs by culture in vitro in a 3D matrix is also disclosed in WO 2010/026575, which is incorporated by reference herein in its entirety. In each of these references, following growth of the ASCs in a 3D matrix the cells are harvested using a procedure that entails multiple washes of the cells and matrix with buffer, followed by release of the cells from the matrix by exposing the cells to a solution of Trypsin EDTA with gentle agitation.

While the harvest procedure described in these references permits one to recover expanded ASCs from a 3D matrix, the characteristics of the matrix lead to inefficiencies in the process. An advantage of a 3D matrix is that it provides a three-dimensional microenvironment in which the cells being cultured are better able to mimic their in vivo counterparts. While the 3D microenvironments in the matrix promote the growth and proliferation of the cultured cells, they also provide interior spaces from which it is difficult to dislodge cells in the harvest process. This difficulty is compounded by the presence of extracellular macromolecules secreted by the cultured cells that serve to attach the cells to the surface of the matrix.

Accordingly, there is a need for cell harvest methods that improve the efficiency of cell recovery from 3D matrices used in bioreactors.

SUMMARY OF THE INVENTION

According to one aspect, there are provided methods for harvesting cells grown in culture comprising growing the cells on an adherent material, wherein the cells are attached to the adherent material, dissociating the cells from the adherent material by exposing them to a dissociating agent, vibrating the adherent material for a period of time at a frequency and amplitude sufficient to release the cells from the adherent material, and recovering the cells. In some embodiments, the methods further comprise vibrating the adherent material for a period of time at a frequency and amplitude sufficient to flush the released cells from the material. In still further embodiments, the adherent material provides a 2-dimensional surface to which the cells attach, while in other embodiments, the adherent material provides a 3-dimensional matrix to which the cells attach.

In some embodiments, the 3-dimensional matrix is enclosed in a packed bed within a bioreactor. In some embodiments, the 3-dimensional matrix comprises a single-piece scaffold, multiple beads, multiple carriers, microfibers, nanofibers, or combinations thereof. In some embodiments, the microfibers or nanofibers are woven or non-woven. In other embodiments, the beads are smooth or porous. In still other embodiments, the microfibers or nanofibers are non-woven.

In some embodiments, the adherent material comprises one or more of a polyester, a polypropylene, a polyalkylene, a polyfluorochloroethylene, a polyvinyl chloride, a polyvinyl fluoride resin, a polystyrene, a polysulfone, a polyurethane, a polyethyene terephtalate, a cellulose, a glass fiber, a ceramic particle, a matrigel, an extracellular matrix component, a collagen, a poly L lactic acid, a dextran, an inert metal fiber, silica, natron glass, borosilicate glass, chitosan, or a vegetable sponge. In particular embodiments, the cellulose is cellulose acetate. In other embodiments, the extracellular matrix component is one or more of fibronectin, vitronectin, chondronectin, or laminin. In some embodiments, the adherent material is electrostatically charged. In some embodiments, the adherent material is coated with collagen or gelatin.

In some embodiments of the method, the dissociating agent is trypsin, papain, elastase, hyaluronidase, collagenase type 1, collagenase type 2, collagenase type 3, collagenase type 4, dispase, or a combination thereof. In particular embodiments, the trypsin is recombinant trypsin.

In some embodiments, the cells are human cells. In some embodiments, the human cells are adherent cells. In still other embodiments, the adherent cells are adherent stromal cells. In some embodiments, the origin of the adherent stromal cells is placenta, adipose tissue, or bone marrow. In particular embodiments, the origin of the adherent stromal cells is placenta. In some embodiments, the adherent stromal cells are obtained from either or both of the fetal or maternal parts of the placenta.

In some embodiments, the adherent material is vibrated by a substantially linear reciprocating motion. In still other embodiments, the reciprocating motion has an amplitude of between about 10 mm to about 750 mm and a frequency of 3 to 6 Hz. In other embodiments, the duration of the reciprocating motion is from about 1 second, 15 seconds, 30 seconds, 1 minute, 2 minutes, 5, minutes, 10 minutes, or 20 minutes. In still other embodiments, the frequency of the reciprocating motion is about 5 Hz and the duration is about 30 seconds or less. In some embodiments, the amplitude is about 25 mm. In other embodiments, the amplitude of the substantially linear reciprocating motion is a distance that is 15-100% of the height of a basket containing the adherent material.

In some embodiments, the harvested cells are characterized by one or more of: at least 50% of cell viability; b) at least 50% of harvest efficiency; c) a vitality index of less than or equal to 0.5; or d) a heterogeneous cell population. Other embodiments comprise cells harvested by any of the methods disclosed herein.

In another aspect, there is provided a method of seeding cells in a 3-dimensional matrix in a bioreactor comprising providing a three-dimensional matrix in a fluid within a container of the bioreactor, introducing a composition comprising cells into the container, vibrating the matrix for a period of time at a frequency and amplitude sufficient to mix the cells throughout the matrix, and discontinuing the vibration to permit the cells to attach to the matrix. In some embodiments, the fluid is a growth medium. In other embodiments, the methods further comprise growing the cells in the bioreactor by applying intermittent vibration to the matrix for a period of time at a frequency and amplitude sufficient to mix the growth medium throughout the matrix.

In some embodiments, the 3-dimensional matrix is enclosed in a packed bed within a bioreactor. In some further embodiments, the 3-dimensional matrix comprises a single-piece scaffold, multiple beads, multiple carriers, microfibers, nanofibers, or combinations thereof. In particular embodiments, the microfibers or nanofibers are woven or non-woven. In other embodiments, the beads are smooth or porous.

In some embodiments, the 3-dimensional matrix comprises an adherent material. In some embodiments, the adherent material comprises one or more of a polyester, a polypropylene, a polyalkylene, a polyfluorochloroethylene, a polyvinyl chloride, a polyvinyl fluoride resin, a polystyrene, a polysulfone, a polyurethane, a polyethyene terephtalate, a cellulose, a glass fiber, a ceramic particle, a matrigel, an extracellular matrix component, a collagen, a poly L lactic acid, a dextran, an inert metal fiber, silica, natron glass, borosilicate glass, chitosan, or a vegetable sponge. In particular embodiments, the cellulose is cellulose acetate. In other embodiments, the extracellular matrix component is one or more of fibronectin, vitronectin, chondronectin, or laminin. In some embodiments, the adherent material is electrostatically charged. In some embodiments, the adherent material is coated with collagen or gelatin.

In some embodiments, the seeded cells are human cells. In some embodiments, the human cells are adherent cells. In still other embodiments, the adherent cells are adherent stromal cells. In some embodiments, the origin of the adherent stromal cells is placenta, adipose tissue, or bone marrow. In particular embodiments, the origin of the adherent stromal cells is placenta. In some embodiments, the adherent stromal cells are obtained from either or both of the fetal or maternal parts of the placenta.

In some embodiments, the 3-dimensional matrix is vibrated by a substantially linear reciprocating motion. In still other embodiments, the reciprocating motion has an amplitude of between about 10 mm to about 750 mm and a frequency of 1 to 3 Hz. In other embodiments, the duration of the reciprocating motion is from about 1 second, 15 seconds, 30 seconds, 1 minute, 2 minutes, 5, minutes, 10 minutes, or 20 minutes. In still other embodiments, the frequency of the reciprocating motion is about 1 Hz and the duration is about 30 seconds or less. In some embodiments, the amplitude is about 25 mm. In other embodiments, the amplitude of the substantially linear reciprocating motion is a distance that is 15-100% of the height of a basket containing the adherent material.

Another embodiment is an apparatus comprising an adherent material in a container, and a vibrator for imparting a reciprocating motion to the adherent material, the vibrator comprising one or more controls for adjusting amplitude and frequency of the reciprocating motion, wherein the vibrator is configured to vibrate in a manner causing cells attached to the adherent material to detach from the adherent material. In some embodiments, the adherent material is a 2D matrix or a 3D matrix, and in particular embodiments is a 3D matrix.

In some embodiments, the apparatus is a bioreactor. In particular embodiments, the bioreactor is a plug flow bioreactor, a continuous stirred tank bioreactor, a stationary-bed bioreactor, an air-lift bioreactor, or a cell seeding perfusion. In some embodiments, the bioreactor is a plug flow bioreactor comprising a packed-bed 3-dimensional matrix and the reciprocating device comprises a basket that substantially envelopes the packed bed.

In some embodiments of the apparatus, the 3-dimensional matrix comprises a single-piece scaffold, multiple beads, multiple carriers, microfibers, nanofibers, or combinations thereof. In particular embodiments, the microfibers or nanofibers are woven or non-woven. In other embodiments, the beads are smooth or porous. In some embodiments of the apparatus, the 3-dimensional matrix comprises one or more of a polyester, a polypropylene, a polyalkylene, a polyfluorochloroethylene, a polyvinyl chloride, a polyvinyl fluoride resin, a polystyrene, a polysulfone, a polyurethane, a polyethyene terephtalate, a cellulose, a glass fiber, a ceramic particle, a matrigel, an extracellular matrix component, a collagen, a poly L lactic acid, a dextran, an inert metal fiber, silica, natron glass, borosilicate glass, chitosan, or a vegetable sponge.

In particular embodiments, the cellulose is cellulose acetate. In other embodiments, the extracellular matrix component is one or more of fibronectin, vitronectin, chondronectin, or laminin. In some embodiments, the adherent material is electrostatically charged. In some embodiments, the adherent material is coated with collagen or gelatin.

In some embodiments, the apparatus further comprises cells. In some embodiments, the cells are human cells. In some embodiments, the human cells are adherent cells. In still other embodiments, the adherent cells are adherent stromal cells. In some embodiments, the origin of the adherent stromal cells is placenta, adipose tissue, or bone marrow. In particular embodiments, the origin of the adherent stromal cells is placenta. In some embodiments, the adherent stromal cells are obtained from either or both of the fetal or maternal parts of the placenta.

In some embodiments, the vibrator of the apparatus imparts a substantially linear reciprocating motion to the adherent material. In still other embodiments, the reciprocating motion has an amplitude of between about 10 mm to about 750 mm and a frequency of 1 to 6 Hz. In other embodiments, the duration of the reciprocating motion is from about 1 second, 15 seconds, 30 seconds, 1 minute, 2 minutes, 5, minutes, 10 minutes, or 20 minutes. In still other embodiments, the frequency of the reciprocating motion is about 5 Hz and the duration is about 30 seconds or less. In other embodiments, the frequency of the reciprocating motion is about 1 Hz. In some embodiments, the amplitude is about 25 mm. In other embodiments, the amplitude of the substantially linear reciprocating motion is a distance that is 15-100% of the height of a basket containing the adherent material.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented as providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF EMBODIMENTS

Figure 1A:
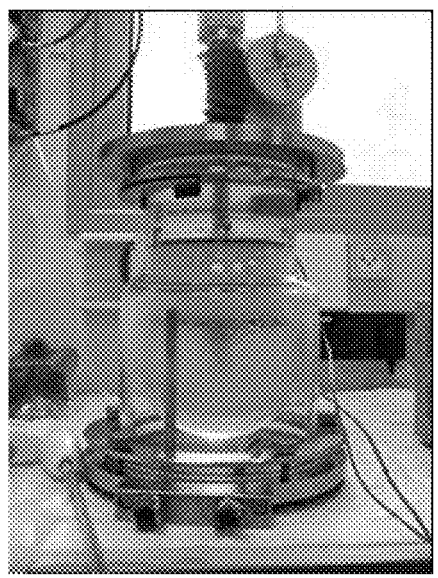
FIGS. 1A and 1B illustrate an embodiment of a reactor with the basket that contains the 3D matrix. This-open system embodiment is used only for the harvesting step.
Figure 1B:
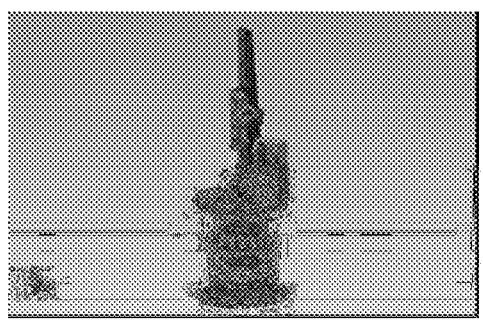
Figure 2:
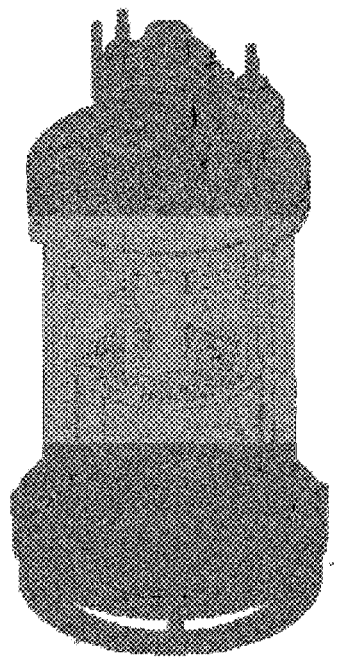
FIG. 2 illustrates another embodiment of the reactor with the basket. This closed-system embodiment is used for both the culturing and harvesting step.
Figure 3:
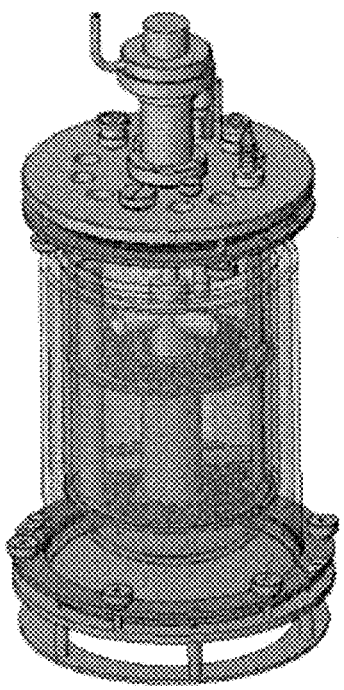
FIG. 3 is another embodiment illustrating the reactor with the basket for use in a closed-system.

In one embodiment, this specification describes a method for using vibration, for example, vibration resulting from a controlled, substantially linear reciprocating motion, to harvest cells grown in vitro. In particular, the cells are grown on an adherent surface, which in some cases is a 3-dimensional matrix. The inventors have recognized that by applying a suitable reciprocating motion that is controlled for both amplitude and frequency cells that grow attached to the adherent material are detached with high efficiency, resulting in recovery of greater quantities of cells compared to existing methods for harvesting cells that are known in the art. In another embodiment, this specification describes using controlled vibration to facilitate seeding cells onto an adherent material prior to their culture in an in vitro system, for example, a bioreactor. Also described is the use of controlled vibration to facilitate mixing of growth medium throughout an adherent material while culturing cells in vitro. Thus, one embodiment disclosed in this specification is an apparatus providing a closed system, for example, a bioreactor configured with a device for imparting a reciprocating motion on a container that contains the adherent material, such that the methods described herein may be performed in a single device. In another embodiment, there is described an open system, which is used to harvest cells that have been grown in vitro on an adherent material. In another embodiment, the specification discloses an apparatus for performing the methods described herein.

The principles and operation of the present invention may be better understood with reference to the drawings and accompanying descriptions. Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Without being limited by theory, the inventors have discovered that the force imparted by vibration, for example, a reciprocating motion that is controlled and substantially linear, may be used to recover cells grown on an adherent material such as a 3D matrix as conventionally used in bioreactor systems for culturing cells in vitro. They have discovered that the mechanical separation of the cells from such carriers is affected by two main forces:
 1. High frequency vibration (3-6 Hz), which generates high moment on the carriers that releases the cells from the porous matrix of the carriers.
 2. Low frequency vibration (1-3 Hz) which generates sufficient circulation inside and outside of the carriers thereby allowing for very efficient mixing with low shear forces.

The inventors have also discovered that the uniform mixing that results from low frequency vibration allows for seeding cells onto carriers and also for efficiently growing cells on the carriers.

It is conventional in the art to use an impeller or similar device to provide agitation and so detach cells from an adherent material. However, shear forces imparted by the circular flow arising from the use of an impeller can damage cultured cells. The inventors have found that by using a controlled reciprocating motion they can minimize the shear forces imparted to the cells while increasing the efficiency of harvesting cells from an adherent material. In some embodiments, using a larger amplitude of movement combined with a lower frequency provides the most efficient release of cells from the adherent material while preserving the integrity and viability of the released cells. The optimal amplitude and frequency of vibration to use for a particular cell type, adherent material, and bioreactor will vary, however, the skilled artisan can readily determine suitable conditions for harvesting cells using vibration by routine trial and error given the teaching of this specification.

In addition to their use with 3D adherent materials, the methods described in this specification may be used with adherent materials that are 2-dimensional. The conditions required to harvest cells using a vibrational motion will vary depending on the nature of the adherent material, and may be readily determined based on the teaching of this specification. For example, in contrast to cell harvest from a 2D adherent material in which the only points of attachment to be broken are between the cells and the vessel in which the cells are growing, in harvesting cells from a 3D adherent material one also needs to detach cells from the extracellular matrix which forms in a manner that is dependent on growth parameters in the culture system. For example, an elongated growth period will result in the formation of more extracellular matrix and will require different harvest conditions as compared to a shorter growth period. Accordingly, the apparatus used to impart the reciprocating motion on the adherent material must be controllable so that the amplitude, frequency and duration of the reciprocating motion may be adjusted to provide for efficient harvest of cells for any given conditions of growth, while also limiting the potential for damage to the cells arising from the forces generated by the reciprocating motion. With respect to potential cell damage, the methods described in this specification provide an advantage over conventional methods in the art because forces are applied to the cells for a shorter duration thereby reducing the amount of stress cells are exposed to during in vitro culture, and in particular, during harvest.

The "closed system" embodiment described herein, which permits one to seed, grow, and harvest the cells in one apparatus or bioreactor system, provides a significant advantage in terms of efficiency and in minimizing the potential for contamination of the harvested cells by permitting all of the steps to be performed in one device.

In one embodiment there is provided a method of harvesting cells expanded by culture in a 3D culture system, more particularly, expanded adherent mammalian cells, for example, cells from placenta, adipose tissue, or bone marrow. In some embodiments, cells are seeded onto the 3D matrix using vibration to distribute the cells within the matrix. In one embodiment, vibration is used after the cells are seeded within the matrix to circulate culture medium through the matrix.

As used herein the terms "expanding" and "expansion" refer to cell growth, that is, increase of a cell population (for example, at least 2 fold) with or without differentiation accompanying such increase.

As used herein, "cells" refers to any mammalian cell capable of being cultured in vitro. In certain embodiments, the cells are human.

As used herein the phrase "adherent cells" refers to a homogeneous or heterogeneous population of cells which are anchorage dependent, that is, require attachment to a surface in order to grow in vitro.

As used herein the phrase "adipose tissue" refers to a connective tissue which comprises fat cells (adipocytes).

As used herein the term "placenta tissue" refers to any portion of the mammalian female organ which lines the uterine wall and during pregnancy envelopes the fetus, to which it is attached by the umbilical cord. Following birth, the placenta is expelled (and is referred to as a post-partum placenta).

As used herein the phrase "three dimensional culturing conditions" refers to a culture in which the cells are cultured under conditions that are compatible with cell growth and that include a matrix that allows cell growth in three dimensions. It is well appreciated that the in situ environment of a cell in a living organism (or a tissue) as a three-dimensional architecture. Cells are surrounded by other cells. They are held in a complex network of extracellular matrix nanoscale fibers that allows the establishment of various local microenvironments. Their extracellular ligands mediate not only the attachment to the basal membrane, but also access to a variety of vascular and lymphatic vessels. Oxygen, hormones and nutrients are ferried to cells and waste products are carried away.

In some embodiments, the adherent material is configured for 3D culturing thereby providing a growth matrix that substantially increases the available attachment surface for the adherence of the cells so as to mimic the infrastructure of the tissue (e.g., placenta).

In other embodiments, the fibers in the 3D matrix form a pore volume as a percentage of total volume of from 40 to 95% and a pore size of from 10 microns to 400 microns. In another embodiment, the matrix has a pore volume as a percentage of total volume of from 60 to 95%.

As used herein, "seeding" means the process of introducing cells into the adherent material, for example, a 3D matrix, such that the cells can attach to the material. In some embodiments, the step of seeding the cells into the bioreactor, for example, a stationary-phase plug-flow bioreactor, is effected while flow in the bioreactor is shut off for at least 10 hours following the seeding. In other embodiments, seeding of the cells is promoted by applying a low frequency vibration, for example, at about 1 to 3 Hz, to the container containing the adherent material such that the medium in the vessel circulates within the adherent material.

As used herein, "harvesting" means removing cells from a 2-dimensional or a 3-dimensional carrier.

In some embodiments for harvesting the cells, the adherent materials are first washed (e.g. 2-3 times) with a saline solution or comparable solution. Subsequent to the washing step, a dissociating step may be conducted on the adherent material. In one example, a suitable dissociation enzyme is employed during the dissociating step.

In another embodiment, the washed adherent materials are washed in the bioreactor. As already mentioned, this is referred to as a closed system. In yet another embodiment, the adherent materials upon which the cells have been grown are transferred to the basket of the harvest system and the basket is placed in a vessel containing a suitable dissociation enzyme, or to which a suitable dissociation enzyme is added. This is an "open system."

In another embodiment, the adherent materials are washed prior to and/or during reciprocating the basket of the bioreactor that contains the carriers. In yet another embodiment, the basket is reciprocated during the complete washing step, intermittently during the wash cycle and/or at the start or end of the wash cycle. In yet another embodiment, the basket is reciprocated during the complete dissociating step, intermittently during the dissociating cycle (e.g. 1 or 2 or 3 or 4 minute cycles) and/or at the start or end of the dissociating cycle.

In one embodiment, the packed bed is reciprocated while simultaneously maintaining the packed bed in a substantially static condition (RELATIVE TO WHAT?) so as to result in at least one of the following: a) at least 80% of cell viability (by the method described in the examples below); b) at least 80% of harvest efficiency (by the method described in the examples below); c) less than or equal to 0.5 vitality index (by the method described in the examples below); and/or d) retaining the heterogeneous composition of the cell population (such that the heterogeneous population of the cell population at the culturing step is substantially similar to the heterogeneous population of the cell population at the harvesting stage. In another embodiment, the packed bed is reciprocated in a substantially linear motion at an amplitude, frequency, and duration sufficient to release the cells from the adherent material.

In another embodiment, the packed bed is reciprocated while simultaneously maintaining the packed bed in a substantially static condition so as to result in at least 70% of cell viability (by the method described in the examples below). In another embodiment, the packed bed is reciprocated while simultaneously maintaining the packed bed in a substantially static condition so as to result in at least 60% of cell viability (by the method described in the examples below). In another embodiment, the packed bed is reciprocated while simultaneously maintaining the packed bed in a substantially static condition so as to result in at least 50% of cell viability (by the method described in the examples below).

In still another embodiment, the packed bed is reciprocated while simultaneously maintaining the packed bed in a substantially static condition so as to result in at least 70% of harvest efficiency (by the method described in the examples below). In another embodiment, the packed bed is reciprocated while simultaneously maintaining the packed bed in a substantially static condition so as to result in at least 60% of harvest efficiency (by the method described in the examples below). In another embodiment, the packed bed is reciprocated while simultaneously maintaining the packed bed in a substantially static condition so as to result in at least 50% of harvest efficiency (by the method described in the examples below).

In some embodiments, the reciprocating condition for the basket of the bioreactor is an amplitude of about 10 mm to about 750 mm (or any integral value within this range). In yet another embodiment, the reciprocating condition for the basket of the bioreactor is a frequency of about 3-6 Hz (e.g. 4, 5), or higher. In another embodiment, the bioreactor dimensions can be 5 liters with a diameter of about 140 mm and a height of 90 mm. In another embodiment, the bioreactor dimensions can be 14 liters with a diameter of about 200 mm and a height of 130 mm. In another embodiment, the bioreactor dimension can be 75 liters. In another embodiments, the bioreactor dimension can be 150 liters. In another embodiment, the reciprocating condition for the basket of the bioreactor is an amplitude of 15-100% of the basket height. In one another embodiment, the basket was reciprocated for about 0.25, 0.5, 1, 5, 10, 20 minutes, or longer.

Placenta-derived adherent stromal cells may be obtained from both fetal (i.e., amnion or chorion) and maternal (i.e., decidua basalis, and decidua parietalis) parts of the placenta. Thus, "maternal" adherent stromal cells from a placenta comprise at least about 70%, 75%, 80%, 85%, 90%, 92%, 94%, 95%, 96%, 98%, 99% or even 100% of cells from a maternal portion of placenta. Similarly, "fetal" adherent stromal cells comprise at least about 70%, 75%, 80%, 85%, 90%, 92%, 94%, 95%, 96%, 98%, 99% or even 100% adherent cells from a fetal portion of placenta.

As used herein, a "dissociating agent" is any compound that serves to disrupt points of attachment between a cell and a surface to which the cell is attached. In some embodiments, the dissociating agent is an enzyme. In particular embodiments, the enzyme is trypsin, including recombinant trypsin, papain, elastase, hyaluronidase, collagenase type 1, collagenase type 2, collagenase type 3, collagenase type 4, or dispase.

Methods of preparing and characterizing maternal-derived and fetal-derived adherent stromal cells are described in WO 2011/064669, which is incorporated by reference. In some embodiments, maternal and fetal placental adherent stromal cells are identified based on genotype and/or karyotype (e.g., FISH or G-banding) analysis. For example, adherent stromal cells from a placenta of a male embryo can be separated into fetal and maternal cells based on karyotype analysis (i.e., XX cells are maternal while XY cells are fetal). In some embodiments, adherent stromal cells derived from a fetal portion of the placenta (e.g., consisting of or comprising chorionic villi) express CD200. That is, at least about 50%, 55%, 60%, 65%, 70%, 75%, 80%, 85%, 90%, 95%, 96%, 97%, 98%, 99% or 100% of the cells express CD200 as measured by flow cytometry using an isotype control to define negative expression. In some embodiments, not more than 3.5%, not more than 3%, not more than 2%, or not more than 1% of the adherent stromal cells from a maternal portion express CD200 as measured by flow cytometry using an isotype control to define negative expression.

Irrespective of whether maternal, fetal, or mixed maternal and fetal-derived placental adherent cells are being prepared, tissue specimens are washed in a physiological buffer [e.g., phosphate-buffered saline (PBS) or Hank's buffer). Single-cell suspensions are made by treating the tissue with a digestive enzyme (see below) or/and mincing and flushing the tissue parts through a nylon filter or by gentle pipetting (Falcon, Becton, Dickinson, San Jose, Calif.) with washing medium.

Adipose tissue derived adherent stromal cells may be isolated by a variety of methods known to those skilled in the art. For example, such methods are described in U.S. Pat. No. 6,153,432. The adipose tissue may be derived from omental/visceral, mammary, gonadal, or other adipose tissue sites. A preferred source of adipose tissue is omental adipose. In humans, the adipose is typically isolated by liposuction.

Isolated adherent stromal cells from adipose tissue may be derived by treating the tissue with a digestive enzyme such as collagenase, trypsin and/or dispase; and/or effective concentrations of hyaluronidase or DNAse; and ethylenediaminetetra-acetic acid (EDTA); at temperatures between 25-50° C., for periods of between 10 minutes to 3 hours. The cells may then be passed through a nylon or cheesecloth mesh filter of between 20 microns to 800 microns.

The cells are then subjected to differential centrifugation directly in media or over a Ficoll or Percoll or other particulate gradient. Cells are centrifuged at speeds of between 100 to 3000×g for periods of between 1 minutes to 1 hour at temperatures of between 4-50° C. (see, e.g., U.S. Pat. No. 7,078,230).

In addition to placenta or adipose tissue derived adherent stromal cells, one may use of adherent stromal cells from other cell sources. For example, in certain embodiments, the adherent stromal cells are obtained from bone marrow. Other tissue sources from which adherent stromal cells can be retrieved include, but are not limited to, cord blood, hair follicles [e.g. as described in Us Pat. App. 20060172304], testicles [e.g., as described in Guan K., et al., Nature. 2006 Apr. 27; 440(7088): 1199-203], human olfactory mucosa [e.g., as described in Marshall, C T., et al., Histol Histopathol. 2006 June; 21(6):633-43], embryonic yolk sac [e.g., as described in Geijsen N, Nature. 2004 Jan. 8; 427(6970): 148-54] and amniotic fluid [Pieternella et al. (2004) Stem Cells 22:1338-1345]. Adherent stromal cells from these tissue sources can be isolated by culturing the cells on an adherent surface, thus isolating adherent stromal cells from other cells in the initial population, which are then harvested according to the methods described herein.

Regardless of the origin (e.g., placenta, adipose tissue, or bone marrow), cell retrieval is generally effected under sterile conditions. Once isolated cells are obtained, they are allowed to adhere to an adherent material (e.g., configured as a surface) to thereby isolate adherent stromal cells. This may be effected prior to or concomitant with culturing in 3D culturing conditions.

As used herein "an adherent material" refers to a synthetic, naturally occurring, or a combination of same, of a non-cytotoxic (i.e., biologically compatible) material having a chemical structure (e.g., charged surface exposed groups) which may retain the cells on a surface.

Examples of adherent materials which may be used in accordance with this aspect of the present invention include, but are not limited to, a polyester, a polypropylene, a polyalkylene, a polyfluorochloroethylene, a polyvinyl chloride, a polyvinyl fluoride resin, a polystyrene, a polysulfone, a polyurethane, a polyethyene terephtalate, a cellulose, a glass fiber, a ceramic particle, a matrigel, an extracellular matrix component, a collagen, a poly-L-lactic acid, a dextran, an inert metal fiber, silica, natron glass, borosilicate glass, chitosan, or a vegetable sponge. In certain embodiments the cellulose is cellulose acetate. In other embodiments, the extracellular matrix component is one or more of fibronectin, vitronectin, chondronectin, or laminin. In still further embodiments, the adherent material is electrostatically charged. In other embodiments, the adherent material is coated with collagen or gelatin.

In one specific example, the adherent material is Fibra-Cel® disks (New Brunswick Scientific). Fibra-Cel disks are composed of polyester non-woven fiber and polypropylene. Fibra-Cel disks are also treated electrostatically to facilitate cells adhering to the disks and becoming trapped in the fiber system, where they remain throughout the process. Fibra-Cel® disks have a surface area per gram of 1200 cm$^2$ and a disk diameter of 6 mm Non-limiting examples of base media useful in culturing according to the present invention include Minimum Essential Medium Eagle, ADC-I, LPM (Bovine Serum Albumin-free), F1O(HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM—without serum), Yamane, IMEM-20, Glasgow Modification Eagle Medium (GMEM), Leibovitz L-15 Medium, McCoy's 5A Medium, Medium M199 (M199E—with Earle's sale base), Medium M 199 (M 199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the present invention is DMEM. These and other useful media are available from GIBCO, Grand Island, N.Y., USA and Biological Industries, Bet HaEmek, Israel, among others. A number of these media are summarized in Methods in Enzymology, Volume LVIII, "Cell Culture", pp. 62 72, edited by William B. Jakoby and Ira H. Pastan, published by Academic Press, Inc.

The medium may be supplemented, for example, with serum such as fetal serum of bovine or other species, and optionally or alternatively supplemented with growth factors, cytokines, and/or hormones (e.g., growth hormone, erythropoeitin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor, fibroblast growth factor, nerve growth factor, cilary neurotrophic factor, platelet derived growth factor, and bone morphogenetic protein at concentrations of between pigogram/ml to milligram/ml levels.

It is further recognized that additional components may be added to the culture medium. Such components may be antibiotics, antimycotics, albumin, amino acids, and other components known to the art for the culture of cells.

Adherent stromal cells may be propagated in vitro by conventional two dimensional (2D) culture conditions or under three dimensional (3D) culture conditions. The phrase "two dimensional culture" or "2D" refers to a culture in which the cells grow primarily in one plane, as in a tissue culture dish.

Once adherent stromal cells are at hand they may be passaged to three dimensional settings. It will be appreciated though that the cells may be transferred to a 3D-configured matrix immediately after isolation. Thus, the adherent material of the 3D aspect of the present invention is configured for 3D culturing thereby providing a growth matrix that substantially increases the available attachment surface for the adherence of the adherent stromal cells so as to mimic the infrastructure of the tissue (e.g., placenta). Further details relating to the fabrication, use and/or advantages of the growth matrix which was used to reduce the present invention to practice are described in U.S. Pat. Nos. 5,168,085 and 5,266,476, both are incorporated herein by reference. In some embodiments, the 3-dimensional matrix comprises a single-piece scaffold, multiple beads, multiple carriers, microfibers, nanofibers, or combinations thereof. In certain embodiments, the microfibers or nanofibers are woven or non-woven. In other embodiments, the beads or smooth or porous.

In some embodiments, the adherent material is in a container. As used herein, a "container" refers to any type of receptacle in which material may be held. In some embodiments, the container holds liquid, such as growth medium, in addition to the adherent material. In some additional embodiments, the container has an inlet and an outlet for passing liquid into and out of the container. In other embodiments, the adherent material is held within an basket that is within the container. In some embodiments, the basket is operatively linked to a vibrator configured to impart vibrational motion to the basket and its contents.

For example, for a growth matrix of 0.5 mm in height, the increase is by a factor of at least from 5 to 30 times, calculated by projection onto a base of the growth matrix. Such an increase by a factor of about 5 to 30 times, is per unit layer, and if a plurality of such layers, either stacked or separated by spacers or the like, is used, the factor of 5 to 30 times applies per each such structure. When the matrix is used in sheet form, it may be non-woven fiber sheets, or sheets of open-pore foamed polymers. The thickness of the sheet can be about 50 µm to 1000 µm, to 2000 µm to 3000 µm, or more, there being provided adequate porosity for cell entrance, entrance of nutrients and for removal of waste products from the sheet. According to one embodiment, the pores have an effective diameter of 10 µm to 400 µm. Such sheets can be prepared from fibers of various thicknesses. In some embodiments, the fiber thickness or fiber diameter range from about 0.5 µm to 100 µm. For example, the fibers can be in the range of 10 µm to 15 µm in diameter. For example, the fibers can be in the range of 30 µm to 40 µm in diameter. For example, the fibers can be in the range of 70 µm to 80 µm in diameter.

The structures of the invention may be supported by, or bonded to, a porous support sheet or screen providing for dimensional stability and physical strength. Such matrix sheets may also be cut, punched, or shredded to provide particles with projected area of the order of about 0.2 mm$^2$ to about 30 mm$^2$, 0.2 mm$^2$ to about 100 mm$^2$, 0.2 mm$^2$ to about 200 mm2, with the same order of thickness (about 50 µm to 3000 µm).

The adherent surface may have a shape selected from the group consisting of squares, rings, discs, and cruciforms. In some embodiments, culturing is effected in a 3D bioreactor.

Examples of such bioreactors include, but are not limited to, a plug flow bioreactor, a continuous stirred tank bioreactor and a stationary-bed bioreactor. For example, a three-dimensional (3D) plug flow bioreactor (as described in U.S. Pat. No. 6,911,201) is capable of supporting the growth and prolonged maintenance of adherent stromal cells. In this bioreactor, adherent stromal cells are seeded on porrosive carriers made of a non-woven fabric matrix of polyester, packed in a glass column, thereby enabling the propagation of large cell numbers in a relatively small volume.

Other 3D bioreactors can be used with the present invention. Another non-limiting example is a continuous stirred tank bioreactor, where a culture medium is continuously fed into the bioreactor and a product is continuously drawn out, to maintain a time-constant steady state within the reactor. A stirred tank bioreactor with a fibrous bed basket is available for example at New Brunswick Scientific Co., Edison, N.J. Other examples include, but are not limited to, a stationary-bed bioreactor, an air-lift bioreactor, [where air is typically fed into the bottom of a central draught tube flowing up while forming bubbles, and disengaging exhaust gas at the top of the column], a cell seeding perfusion bioreactor with polyactive foams [as described in Wendt, D. et al., Biotechnol Bioeng 84: 205-214, (2003)], and tubular poly-L-lactic acid (PLLA) porous scaffolds in a Radial-flow perfusion bioreactor [as described in Kitagawa et al., Biotechnology and Bioengineering 93(5): 947-954 (2006)]. Other bioreactors which can be used in accordance with the present invention are described in U.S. Pat. Nos. 6,277,151, 6,197,575, 6,139,578, 6,132,463, 5,902,741 and 5,629,186. In another embodiment, a plurality of bioreactors may be utilized in parallel or in series orientation.

The matrix used in the bioreactor can, for example, be in the form of a sheet. This sheet may be a non-woven fiber sheet, or a sheet of open-pore foamed polymers. The thickness of the sheet is, in some embodiments, from about 50 µm to 3000 µm or more, there being provided adequate porosity for cell entrance, entrance of nutrients, and for removal of waste products from the sheet.

In some embodiments, cell seeding is effected using 1,000-10,000 cells/cm$^2$ at seeding.

Culturing of the adherent cells in the 3D culture can be effected under a continuous flow of a culture medium. Passaging may also be effected to increase cell number. It will be appreciated that culture medium may be changed in order to prolong and improve culturing conditions. According to an embodiment of the present invention, the cell culturing is effected under perfusion of the culture medium. Typically, the perfusion rate is determined by the glucose concentration in the culture medium of the adherent cells. Thus, according to the present teachings, the culture medium may be changed when the glucose concentration is about 500 mg/L, about 550 mg/L; or about 600 mg/L. In another embodiment the culture medium may be changed when the glucose concentration is between 200-1000 mg/L.

In some embodiments, the culturing of the cells is effected for at least 3, 4, 5, 6, 7, 8, 9, 10, 11, 12, 13, 14, or 20 days, or longer. It will be appreciated that culturing in a bioreactor may prolong this period.

In another embodiment, the adherent stromal cells of the stromal cell culture are grown to a density of at least 1,000 cells per a cubic centimeter of the adherent material. In other embodiments, the adherent stromal cells of the stromal cell culture are grown to a density of at least 5,000 cells per a cubic centimeter of the adherent material. In still other embodiments, the stromal cells of the stromal cell culture are grown to a density of at least 10,000 cells per a cubic centimeter of the adherent material. In still other embodiments, the stromal cells of the stromal cell culture are grown to a density of at least 20,000 cells per a cubic centimeter of the adherent material. In still other embodiments, the stromal cells of the stromal cell culture are grown to a density of at least 30,000 cells per a cubic centimeter of the adherent material. In still other embodiments, the stromal cells of the stromal cell culture are grown to a density of at least 40,000 cells per a cubic centimeter of the adherent material. In other embodiments, the cells are grown up to a density of 100,000 cells per cubic centimeter.

In another embodiment, cells are cultured for a period of time facilitating 2 to 8 cell population doublings.

In another embodiment, cells are harvested according to cell density evaluated according to capacitance evaluated by Biomass monitoring.

In another embodiment, cells are harvested according to cell density evaluated according to Glucose Consumption Rate (GCR).

The cells seeded, grown, and/or harvested by the methods described herein may be adherent stromal cells (ASC). Thus, for example, the cells may have a spindle shape. Alternatively or additionally the cells may express a marker or a collection of markers (e.g. surface marker) typical to adherent stromal cells. Examples of adherent stromal cell surface markers (positive and negative) include but are not limited to CD105+, CD29+, CD44+, CD73+, CD90+, CD34−, CD45−, CD80−, CD19−, CD5−, CD20−, CD11B−, CD14−, CD19−, CD79−, HLA-DR−, and FMC7−. Other adherent stromal cell markers include but are not limited to tyrosine hydroxylase, nestin and H-NF.

In certain embodiments, bone marrow (BM) adherent stromal cells are grown in a 3D culture system and harvested according to the methods disclosed herein. BM cells may be obtained by any known procedure. For example, BM cells may be obtained from aspirated sterna marrow of hematologically healthy donors undergoing open-heart surgery or BM biopsy. Marrow aspirates are diluted three-fold in, for example, Hank's Balanced Salts Solution (HBSS; GIBCO BRL/Invitrogen, Gaithersburg Md.) and subjected to Ficoll-Hypaque (Robbins Scientific Corp. Sunnyvale, Calif.) density gradient centrifugation. Thereafter, marrow mononuclear cells ($<1.077$ gm/cm$^3$) are collected, washed 3 times in HBSS and resuspended in growth media [DMEM (Biological Industries, Beit Ha'emek, Israel) supplemented with 10% FCS (GIBCO BRL), $10^{-4}$ M mercaptoethanol (Merck, White House Station, N.J.), Pen-Strep-Nystatin mixture (100 U/ml:100 ug/ml:1.25 un/ml; Beit Ha'Emek), 2 mM L-glutamine (Beit Ha'Emek)]. Cells from individual donors are incubated separately in tissue culture flasks (Corning, Acton, Mass.) at 37° C. (5% $CO_2$) with weekly change of culture media. Cells are split every 3-4 days using 0.25% trypsin-EDTA (Beit Ha'Emek). Following 2-40 passages, when reaching 60-80% confluence, cells are collected for culturing in a 3D bioreactor.

In other embodiments, cells obtained from placenta are grown in a 3D culture system and harvested according to the methods disclosed herein. Placenta cells may be obtained by any method known in the art. For example, cells may be derived from the inner parts of a full-term delivery placenta. Appropriate sections of the placenta are cut under sterile conditions, washed 3 times with Hank's Buffer, and incubated for 3 h at 37° C. with 0.1% Collagenase (1 mg/ml tissue; Sigma-Aldrich, St. Louis, Mo.). Using gentle pipetting, suspended cells are then washed with DMEM supplemented with 10% FCS, Pen-Strep-Nystatin mixture (100 U/ml:100 ug/ml:1.25 un/ml) and 2 mM L-glutamine, seeded in 75 cm$^2$ flasks and incubated at 37° C. in a tissue culture incubator under humidified condition with 5% $CO_2$. Thereafter, cells are allowed to adhere to a plastic surface for 72 hours after which the media was changed every 3-4 days. When reaching 60-80% confluence (usually 10-12 days), cells are detached from the growth flask using 0.25% trypsin-EDTA and seeded into new flasks. Cultured cells are then collected for culturing in a 3D bioreactor.

In still other embodiments, adherent stromal cells obtained from adipose tissue using techniques known in the art are grown in a 3D culture system and harvested according to the methods disclosed herein. For example, adherent stromal cells may be isolated from human adipose tissue obtained from liposuction procedures. The adipose tissue is washed extensively with equal volumes of PBS and digested at 37° C. for 30 min with collagenase (20 mg/ml). Cells are then washed with DMEM containing 10% FCS, Pen-Strep-Nystatin mixture (100 U/ml:100 ug/ml:1.25 un/ml) and L-Glutamin and centrifuged at 1200 rpm for 10 min RT, resuspended with lysing solution (1:10; Biological Industries, Beit Ha'emek, Israel, to lyse red-blood cells) centrifuged and resuspended with DMEM containing 10% FCS, Pen-Strep-Nystatin mixture (100 U/ml:100 ug/ml:1.25 un/ml) and L-Glutamin. Washed cells are then seeded in a sterile tissue culture medium flask at $3$-$10\times10^7$ cells/flask. The following day cells are washed with PBS to remove residual RBC and dead cells. The cells are kept at 37° C. in a tissue culture incubator under humidified condition with 5% $CO_2$. The medium is changed every 3 to 4 days. At 60-80% confluence, the cells are detached from the growth flask using 0.25 trypsin-EDTA and seeded into new flasks. Following 2-40 passages, when cells reached 60-80% confluence they are collected for culturing in a 3D bioreactor.

Any bioreactor system is suitable for 3D culture of the adherent BM, placenta, or adipose cells described above. For example, in one embodiment one may use a Plug Flow bioreactor as described in U.S. Pat. No. 6,911,201. This bioreactor may be loaded, for example, with 1-100 ml of packed 3D porrosive carriers (4 mm in diameter) made of a non woven fabric matrix of polyester. These carriers enable the propagation of large cell numbers in a relatively small volume. The bioreactor may be maintained in an incubator of 37° C., with a flow rate regulated and monitored by a valve and peristaltic pump. The bioreactor may contain a sampling and injection point allowing for the sequential seeding of cells. Culture medium may be supplied at any suitable pH, for example, pH 6.7-7.4, from a reservoir. The reservoir may be supplied by a filtered gas mixture containing air/$CO_2$/$N_2$/$O_2$ at differing proportions depending on cell density in the bioreactor. The $O_2$ proportion may be adjusted to achieve the desired level of dissolved $O_2$ at the bioreactor exit, as determined by a monitor. The gas mixture may be supplied to the reservoir via silicone tubes or a diffuser. Circulation of the medium may be achieved, for example, by a peristaltic pump.

In one embodiment, non-confluent primary human adherent stromal cell 2D cultures (for example, the BM, placenta, or adipose cells described above), grown as described above, are trypsinized, washed, resuspended in DMEM supplemented with 10% FBS, Pen-Strep-Nystatin mixture (100 U/ml:100 ug/ml:1.25 un/ml) and 2 mM L-glutamine, seeded ($10^3$-$10^5$ cells/ml) via the injection point onto the 3D carriers in a sterile Plug Flow bioreactor. Prior to inoculation, the bioreactor is filled with a suitable buffer, such as PBS-Ca—Mg, autoclaved (120° C., 30 min) and washed with Dulbecco's growth medium containing 10% heat-inactivated fetal calf serum and a Pen-Strep-Nystatin mixture (100 U/ml:100 ug/ml:1.25 un/ml). Flow of the medium within the bioreactor may be adjusted to any suitable rate, for example, a rate of 0.1-5 ml/min. The process of seeding cells in the matrix may be achieved, for example, by stopping medium circulation for 2-48 hrs to allowing the cells to settle on the carriers. The bioreactor is kept at a controlled temperature (37° C.) and pH conditions (pH=6.7-7.8); using an incubator supplied with sterile air and $CO_2$ as needed. Growth medium is replaced as necessary, for example, 2-3 times a week. Circulation medium is replaced with fresh DMEM media, every 4 hr to 7 days. Once the cells have grown to a suitable concentration they may be harvested according to the methods described herein.

As used herein, a "vibrator" means any device that is capable of causing vibration. "Vibration" means mechanical oscillations about an equilibrium point. The oscillations may be periodic or random. In one embodiment, the vibration is due to reciprocating linear oscillations that are controlled with respect to amplitude and frequency. In some embodiments, the amplitude and frequency of the oscillations are constant, while in other embodiments either or both of the amplitude or frequency may be varied as desired to achieve a particular result. In still other embodiments, the duration of the period of time for the vibrations is also controlled using means and devices that are conventional in the art. In some embodiments, the vibrator is an electro-mechanical device, for example, an electric motor with an unbalanced mass on its driveshaft. In other embodiments, the vibrator is an electrical device. Devices capable of imparting vibrations are known in the art and it is well within the skill in the art to adapt existing vibrators in a manner suitable for use in the methods described herein.

Figure 4A:
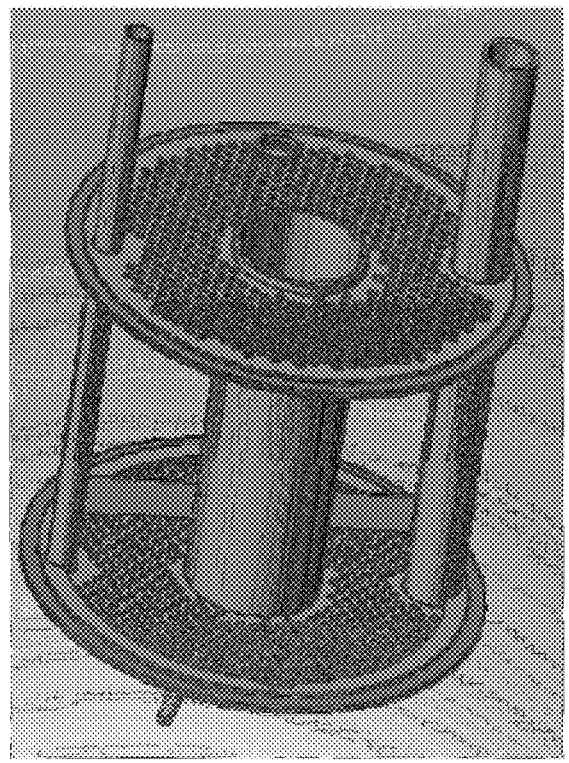
FIG. 4A illustrates an embodiment of the basket design showing a basket without the integral outer walls.
Figure 4B:
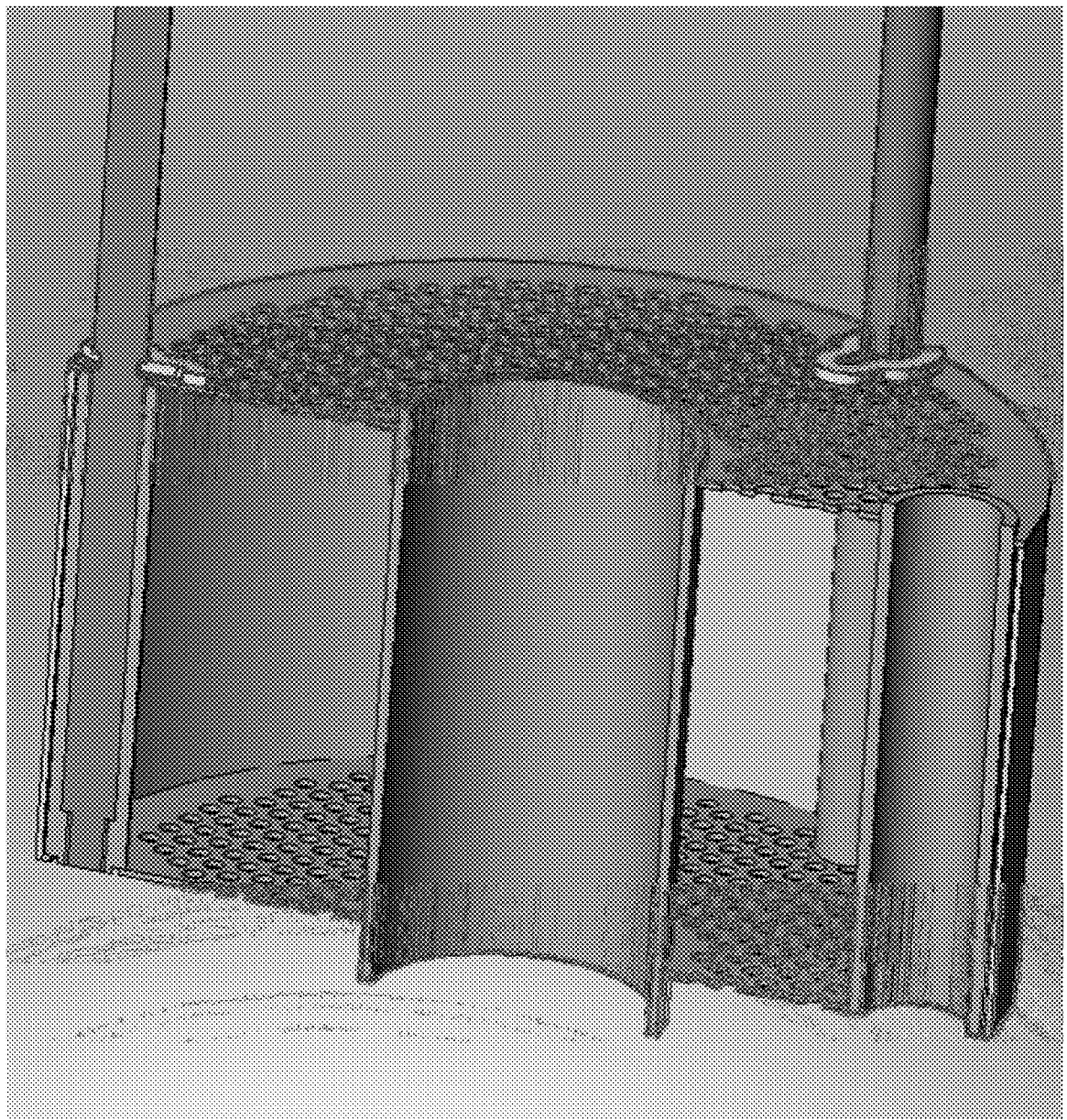
FIG. 4B is a cut-away view of FIG. 4C showing another embodiment of a basket design illustrating a basket with the integral outer wall.
Figure 4C:
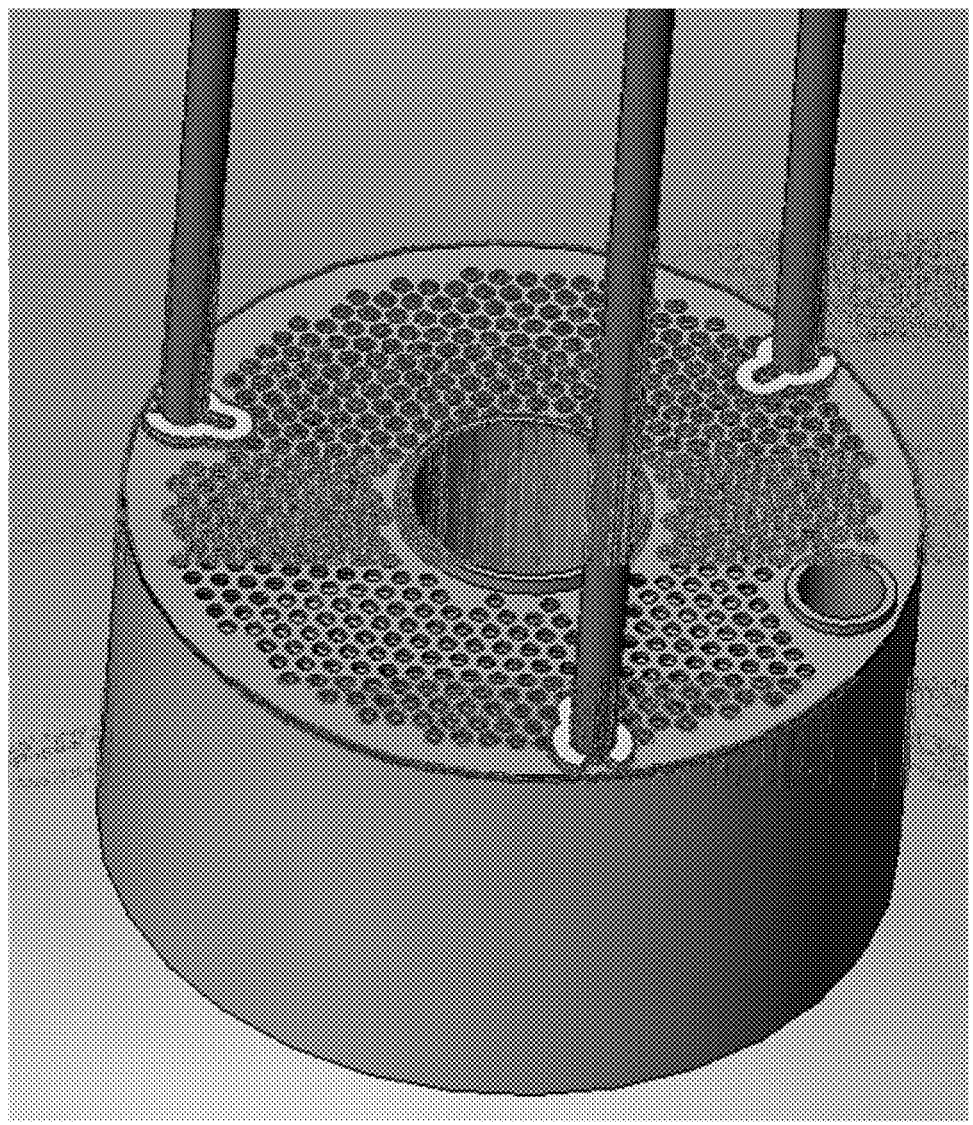
Figure 5:
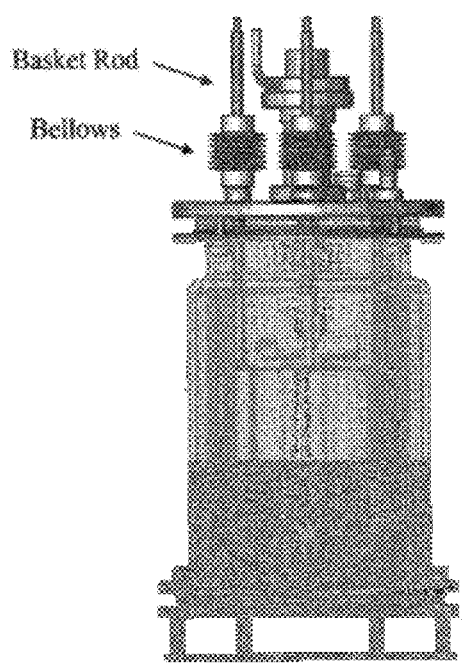
FIG. 5 is a side view of an embodiment of the reactor illustrating the basket rods and bellows that cooperate in the reciprocating movement of the basket within the reactor.
Figure 6:
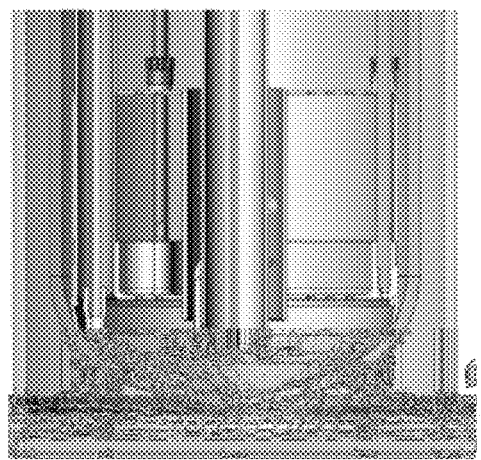
FIG. 6 illustrates a cut-away view of a portion of the reactor with basket demonstrating one embodiment of a sealing mechanism.
Figure 7:
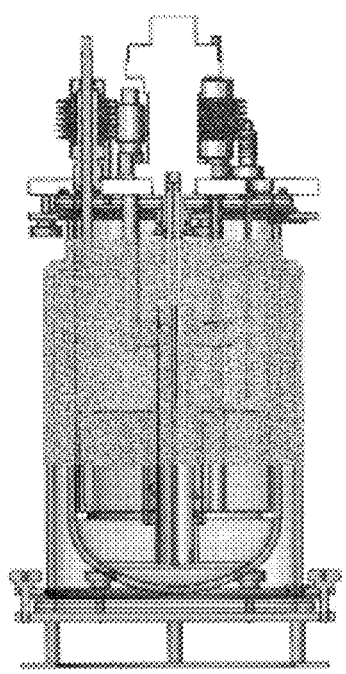
FIG. 7 is another embodiment of the reactor and basket design with a cut-away view illustrating the rod seal design that cooperates with the reciprocating means for moving the basket.
Figure 8:
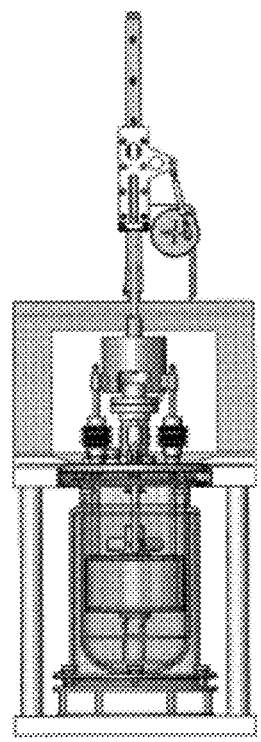
FIG. 8 is an embodiment illustrating the reciprocating device for reciprocating the basket.
Figure 9:
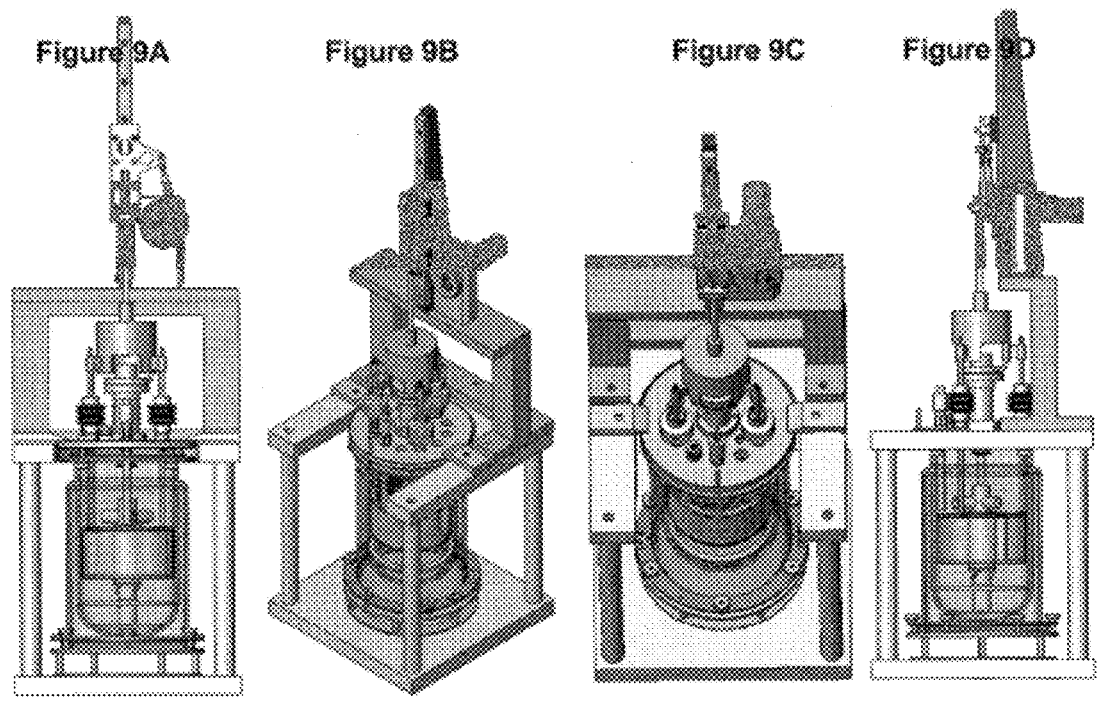
FIGS. 9A, 9B, 9C and 9D are various overhead views of an embodiment of the reciprocating device.

A vibration harvest system was developed by Pluristem. This particular embodiment of the vibration harvest system was designed for a 5 liter bioreactor (New Brunswick Scientific) and is composed of a vibration system (as shown in FIGS. 9A-D) and newly-designed basket (as shown in FIG. 6) that will hold 100 g of FibraCel®. In this embodiment, and referring to FIG. 6, the basket includes a wall located perpendicularly to a top screen and a bottom screen, each screen having perforations therein. The 3D matrix is contained within the space formed enclosed by the wall and top and bottom screens. Either or both screens may be configured such that they may be removed from the basket to permit access to space that contains the 3D matrix. The basket also includes a basket seal for providing a seal between the perimeter of the basket and the inner surface of the bioreactor vessel or container. As shown in FIGS. 4A and 4B the basket may contain one or more passageways, either centrally or distally located, in which components of the bioreactor, for example, a drain tube or impeller, may be located.

Attached to the basket are a plurality of basket rods extending from the basket to the exterior of the bioreactor vessel or container through which a functional connection is made with the vibrator. In this embodiment, the container is sealed with a plate having holes through which the basket rods pass. At the exterior of the plate, the each basket rod passes through a bellows configured to accommodate the reciprocating motion imparted by the vibrator and to provide a seal preventing contaminants from entering the vessel or container.

As used herein the term "about" refers to ±10%.

The terms "comprises," "comprising," "includes," "including," and "having," mean including but not limited to.

The term "consisting of" means including and limited to.

As used herein, the singular form "a", "an" and "the" include plural references unless the context clearly dictates otherwise. For example, the term "a compound" or "at least one compound" may include a plurality of compounds, including mixtures thereof.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

EXAMPLES

Reference is now made to the following examples, which together with the above descriptions illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory 30 Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and 10 Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for 15 Protein Purification and Characterization—A Laboratory Course Manual" CSHL Press (1996).

Cell Culture Growth Procedure in 3D Bioreactor:

Cells were grown in 3D culture using a RALF bioreactor system. The RALF bioreactor is a round-bottomed, double-jacketed glass vessel with a total volume of 3.7 liters made by BioEngineering.

Prior to seeding in the bioreactor, $180\pm30\times10^6$ cells from the 2D stage were thawed and diluted 1:3 with medium (DMEM with 10% FBS and 25 mM HEPES). A sample was taken and cells were counted using a Trypan Blue stain to determine cell number and viability. The cell suspension was transferred under a laminar flow hood into a 0.5 L seeding bottle. From the seeding bottle, the cell suspension was transferred by gravity via sterile tubing into the bioreactor.

The bioreactor contained $1.8\pm0.1$ L medium (DMEM with 10% FBS and 25 mM HEPES) and 30-40 grams of carriers (FibraCel® disks, New Brunswick Scientific). These carriers are made of polyester and polypropylene. The medium in the bioreactor was kept at the following conditions: 37° C., 70% dissolved oxygen ("DO") and pH 7.3. Filtered gases (air, $CO_2$, $N_2$ and $O_2$) were supplied as determined by the control system of the bioreactor to keep the DO value at 70% and the pH value at 7.3. Media circulates in the bioreactor by means of a hollow impeller tube with discharge ports positioned above the basket that holds the carriers. As with the Cell-lift impeller, rotation of these discharge ports creates a low differential pressure at the base of the impeller tube, which circulates media throughout the system.

For the first 4 hours, the medium was agitated at 50 revolutions per minutes (RPM) and increased up to 200 RPM by day 2. For the first 2-3 days, the cells were grown in batch mode. Perfusion was initiated when the medium glucose concentration decreased below 550 mg/liter. The perfusion was adjusted on a daily basis to keep the glucose concentration constant at approximately $550\pm50$ mg\liter. A sample of the growth medium was taken every 1-2 days for glucose, lactate, glutamine, glutamate and ammonium concentration determination (BioProfile 400 analyzer, Nova Biomedical). Cells were cultured in the bioreactors for 6-7 days.

Harvest From the 3D Carriers Using a Marine-Type Impeller (Agitation):

The cell harvest process started at the end of the growth phase (6-7 days). The bioreactor vessel was emptied by gravity via tubing to a waste container. The vessel was opened by removing the head plate and the carriers were transferred to the bottom of the vessel. The Cell-lift impeller was replaced with a sterile marine-type impeller. The marine-type impeller produces an axial flow for applications that require gentle mixing without causing cell damage due to unidirectional flow.

The bioreactor vessel was then closed and refilled with 1 liter pre-warmed (37° C.) PBS. The agitation speed was set to 200 RPM for 2 minutes. The PBS was then drained via tubing by pressure or gravity to the waste bottle. The washing procedure was repeated for three times.

To release the cells from the carriers, 1 liter of pre-warmed (37° C.) recombinant trypsin solution (TrypLE; GIBCO) was added to the bioreactor vessel and the carriers were incubated for 15 minutes. During this incubation the carriers were agitated for 1 minute at 200 RPM in every 5 minutes. The cell suspension was then collected into a 2 liter sterile container containing 200 ml FBS. This step was repeated with pre-warmed (37° C.) TrypLE for 10 minutes (carriers were agitated for 1 minute at 200 RPM every 4 minutes). To wash the detached cells from the carriers, 1 liter of medium was added to the bioreactor vessel and the carriers were agitated at 200 RPM for 2 minutes.

Cell suspension from the three steps was combines and then divided into 500 ml sterile centrifuge tubes. The cells were concentrated by centrifugation, and counted.

Harvest From the 3D Carriers Using the Harvest System Prototype (Vibration):

The cell harvest process started at the end of the growth phase (6-7 days). The bioreactor vessel was emptied by gravity via tubing to a waste container. The vessel was opened by removing the head plate, the basket containing the carriers was opened, and the 3D carriers were transferred, using sterile forceps, from the basket to a sterile glass beaker. The carriers were washed 2-3 times with 1 liter of pre-warmed (37° C.) PBS. The washed carriers were transferred to the basket of the harvest system (prototype), and the basket containing the washed carriers was placed in a 2.2 liter vessel containing 1.8 liters of pre-warmed (37° C.) TrypLE. During this incubation in TrypLE (1-32 min) the basket was vibrated at low frequency (0.7 Hz) to ensure even mixing of the trypsin solution throughout the basket. In order to release the cells from the carriers (harvest stage) the basket was vibrated for 1 minute every 3-8 minutes, using amplitude of 12 mm or 25 mm and a frequency of 3 Hz or 6 Hz, as specified. During the harvest stage, samples of 5 ml cell suspension were collected, at different time points, to a 50 ml centrifuge tube containing 1 ml FBS. The cell suspension was centrifuged, the cell pellet was suspended in 1 ml medium and counted or the total cell suspension was divided to 500 ml sterile centrifuge tubes, cells were centrifuged, re-suspended and counted.

Cell Samples Cryopreservation:

Cells were cryopreserved at concentration of $10\times10^6$ cells/ml in 3D freezing solution (PlasmaLyte, Baxter) with 10% DMSO (Wak-Chemie, GMBH) and 5% Human Serum Albumin (Biotest Pharma, GMBH)] for post thaw viability and vitality assessment.

Cell Number:

Cell number after harvesting was measured by the Trypan blue exclusion method, using the Cedex (Roche Applied Science—Innovatis) or the Countess (Life Technologies—Invitrogen) instruments.

Viability:

Viability was measured by the Trypan Blue exclusion method, using the Cedex instrument or the hemocytometer.

Harvest Efficiency:

The number of cells attached to the FibraCel carriers was assessed, before and after harvest, using the 3-[4,5-Dimethylthiazol-2-yl]-2,5-diphenyltetrazolium bromide (MTT) assay O.D. Harvest efficiency was calculated according to the following formula:

$$\frac{OD \text{ value before harvest} - OD \text{ value after harvest}}{OD \text{ value before harvest}} \times 100$$

The value represents the percentage of cells removed from the carries after harvest (high value=high harvest efficiency and vice versa).

Vitality:

Cells were thawed, seeded into wells of 24 well plates (10,000 cells/well/ml) and grown for 1 and 4 days. Post-thaw vitality was assessed using the MTT assay O.D. Each sample was tested in triplicate.

Experimental Results

Example 1

At the end of growth phase the carriers were washed as described above and transferred to the harvest system basket. The carriers were incubated in TrypLE for 32 minutes while vibrating the basket at low frequency (0.7 Hz). Every 3 minutes the basket was vibrated for 1 minute at a different frequency (Hz) and amplitude (mm), as specified in Table 1. At each time point a sample of 5 ml cell suspension was collected to a 50 ml centrifuge tube and the number of cell was counted using the Cedex instrument.

TABLE 1

Harvest system parameters

| Time (minute) | 4 | 8 | 12 | 16 | 20 | 24 | 28 | 32 |
|---|---|---|---|---|---|---|---|---|
| Voltage (volt) | 24 | 24 | 31.1 | 7.1 | 13.4 | 14.2 | 14.2 | 14.2 |
| Frequency (Hz) | 6 | 6 | 7.8 | 1.8 | 3.4 | 3.6 | 3.6 | 3.6 |
| Amplitude (mm) | 12 | 12 | 12 | 25 | 25 | 25 | 25 | 25 |
| Basket position | high | high | high | high | low | low | low | low |

Figure 10:
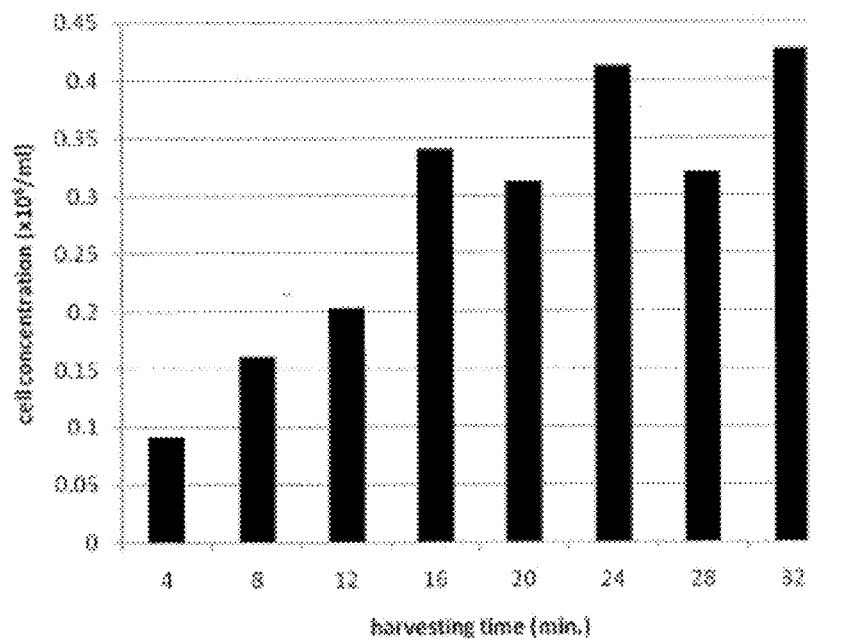
FIG. 10 shows cell concentration data for cells harvested by vibration under different conditions of amplitude and frequency of vibration as set forth in Table 1.

The effect of the harvesting parameters (time, frequency, and amplitude) on the cell concentration in the harvesting liquids are shown in FIG. 10. Although amplitude was changed during the incubation period (after 16 minutes), the results show that using an amplitude of 25 mm, compared to 12 mm, was more efficient in harvesting the cells.

Example 2

At the end of growth phase (6 days) the carriers were washed and transferred to the harvest system basket. The carriers were incubated in TrypLE for 20 minutes while moving the basket at amplitude of 25 mm and low frequency (0.7 Hz). Every 4 minutes the basket was vibrated for 1 minute at amplitude of 25 mm and a frequency of 6 Hz. At each time point, a sample of 5 ml cell suspension was collected to a 50 ml centrifuge tube containing 1 ml FBS. The cell suspension was centrifuged and the cells resuspended in 1 ml of medium (DMEM with 10% FBS and 25 mM HEPES) and counted using the Cedex instrument.

Figure 11:
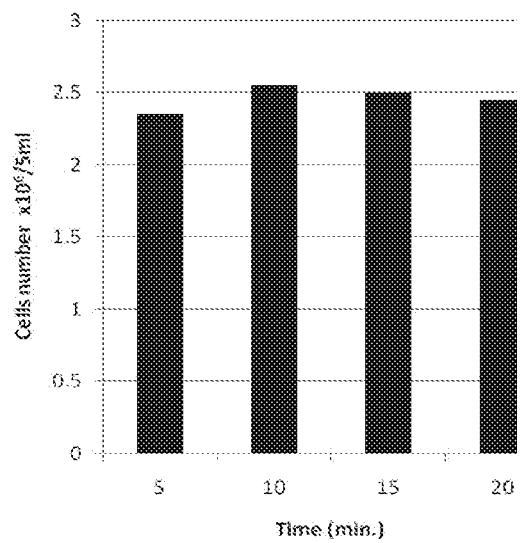
FIG. 11 shows cell concentration data for cells harvested from 3D carriers by vibration (25 mm amplitude, 6 Hz, 1 minute) in an open system.

The effect of harvesting time on the cell number in the 5 ml sample is shown in FIG. 11. It can be seen that when the harvest system was operated in amplitude of 25 mm and frequency of 6 Hz, the number of cells counted in the solution after 5 min was not increased over time.

In another experiment, the carriers were sampled at the end of the growth phase (before harvest) and at the end of the harvesting procedure using the harvest system prototype (amplitude of 25 mm, 6 Hz frequency, duration of 20 minutes). The number of cells attached to the FibraCel carriers was assessed using the MTT assay. The harvest efficiency value represents the percentage of cells removed from the carries at the end of the harvesting procedure based on the O.D. results of the MTT assay.

Figure 12:
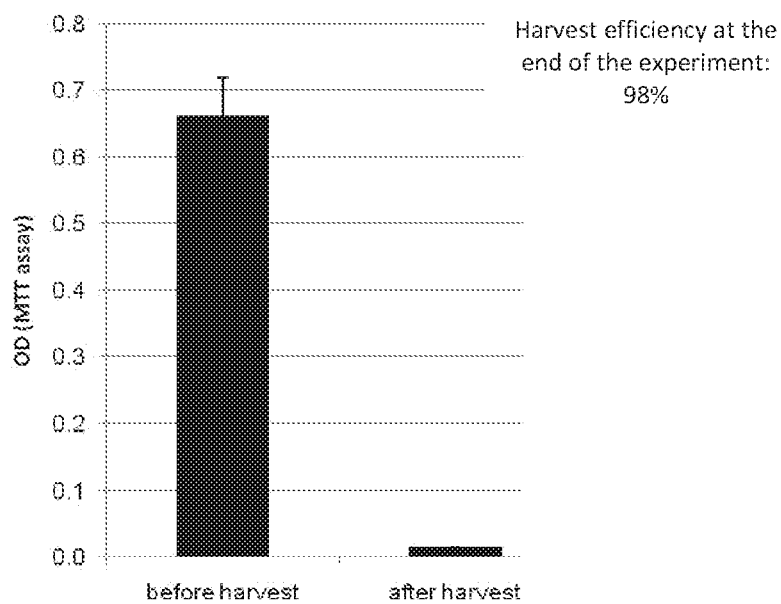
FIG. 12 shows the harvest efficiency from carriers as determined based on optical density using the MTT assay. The carriers were vibrated at 25 mm amplitude, 6 Hz for 20 minutes to detach the cells, yielding a harvest efficiency of 98%.

The MTT assay results of carriers before and after the harvest procedure (FIG. 12) show that the harvest efficiency was 98%.

Example 3

At the end of the growth phase (7 days), the carriers were washed and transferred to the harvest system basket. The carriers were incubated in TrypLE for 8 minutes while shaking the basket at amplitude of 25 mm at low frequency (0.7 Hz). After 8 minutes of incubation the basket was shaken for 1 minute at an amplitude of 25 mm in a frequency of 3 Hz or 6 Hz, as specified. At each time point, a sample of 5 ml cell suspension was collected to a 50 ml centrifuge tube containing 1 ml FBS. The cell suspension was centrifuged, and the cells were resuspended in 1 ml of medium and counted using the Countess instrument.

Figure 13:
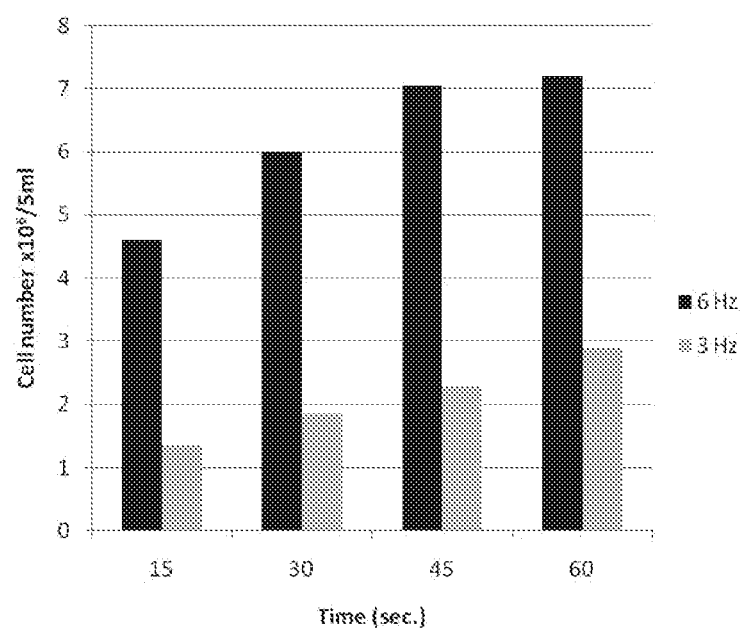
FIG. 13 shows cell concentration data for cells harvested from 3D carriers by vibration (25 mm amplitude for 1 minute) at frequencies of 3 or 6 Hz.

The effect of harvesting frequency and time on the cell number in a 5 ml sample is shown in FIG. 13. It was found that during 1 min. in amplitude of 25 mm, frequency of 6 Hz was more efficient in harvesting than frequency of 3 Hz.

Figure 14:
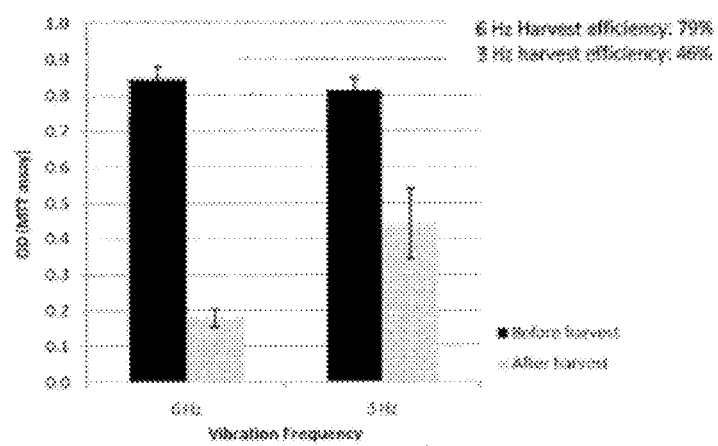
FIG. 14 shows the harvest efficiency from carriers as determined based on optical density using the MTT assay. The carriers were vibrated at 25 mm amplitude for 1 minute at either 3 or 6 Hz to detach the cells. The harvest efficiency at 3 Hz was 46%, while the harvest efficiency at 6 Hz was 79%.

In another experiment, the carriers were sampled at the end of the growth phase (before harvest) and at the end of the harvesting procedure. The number of cells attached to the FibraCel carriers before harvest and after harvest using frequencies of 3 Hz or 6 Hz was assessed using the MTT assay as shown in FIG. 14. The harvest efficiency value represents the percentage of cells removed from the carries after harvest, using frequencies of 3 Hz or 6 Hz, based on the OD results of the MTT assay. In correlation with the cell number, shown in FIG. 13, it can be seen that harvest efficiency with frequency of 6 Hz (25 mm amplitude, 1 min) was higher than with frequency of 3 Hz.

Figure 15:
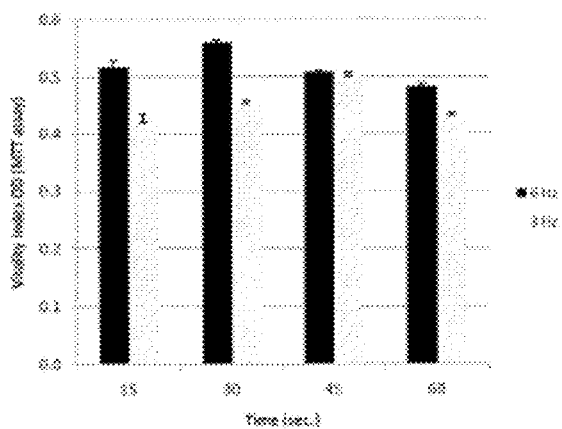
FIG. 15 shows the vitality index for cells harvested from 3D carriers by vibration using a frequency of 3 or 6 Hz.

Cells from each group (frequency of 6 Hz or 3 Hz) were sampled at each time point and were cryopreserved. Cells were thawed, seeded with a concentration of 10,000 cells/ml/well in 24 well plates. The plates were incubated in a humidified incubator at 37° C. and 5% $CO_2$ for 4 days. The post-thaw vitality of the cells was assessed using the MTT assay O.D. (FIG. 15).

According to the post-thaw vitality of the cells, higher frequency (6 Hz) applied during one minute did not harm the cells more than the low frequency of 3 Hz.

Example 4

At the end of growth phase (7 days), cells from each bioreactor system were harvested by agitation, using a marine-type impeller, or by vibration (8 minute incubation in TrypLE, 0.7 Hz in amplitude of 25 mm, followed by a 1 minute vibration at 6 Hz in amplitude of 25 mm). Cell suspension from each harvesting procedure was divided into 500 ml sterile centrifuge tubes, the cells were centrifuged and resuspended, and the total cell numbers were counted using the Countess instrument. As shown in the following table, the vibration procedure of the invention released more cells from the matrix compared to using an impeller to agitate the carriers.

| | Harvest method | |
|---|---|---|
| | Agitation | Vibration |
| Total cell number | $421 \times 10^6$ | $1,045 \times 10^6$ |

Figure 16:
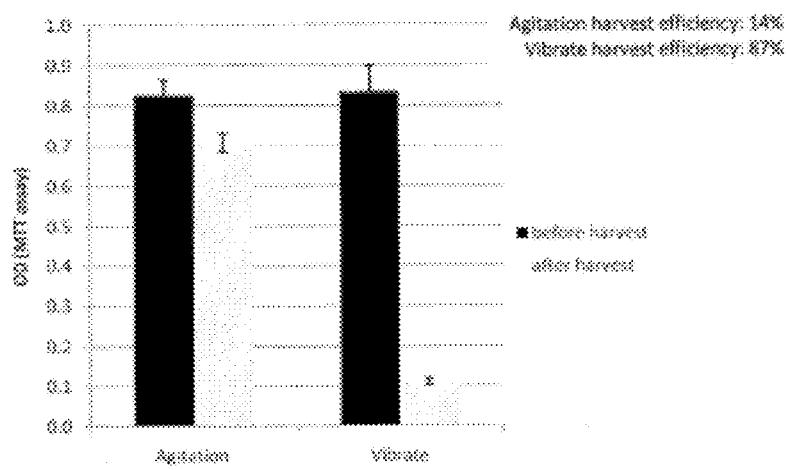
FIG. 16 shows the harvest efficiency from carriers as determined based on optical density using the MTT assay. Cells were harvested from the carriers either by agitation (14% efficiency) or vibration (87% efficiency).

In another experiment, the carriers were sampled from each bioreactor system at the end of growth phase (before harvest) and at the end of the agitation or vibration harvesting procedure. The number of cells attached to the FibraCel carriers was assessed using MTT assay O.D. The harvest efficiency value represents the percentage of cells removed from the carries after harvest by agitation or vibration based on the O.D. results of the MTT assay (FIG. 16). The harvest efficiency was higher using the vibration system (87%) than the harvest efficiency using the agitation method (14%).

Figure 17:
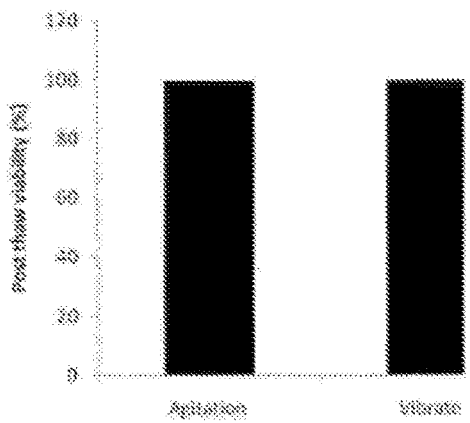
FIG. 17 shows the viability of cells harvested by either agitation or vibration following cryopreservation.

The cells harvested by each of the methods (agitation or vibration) were cryopreserved. The cells were thawed and the post-thaw viability of the cells was assessed with the Trypan Blue dye exclusion method using the hemocytometer. The effect of harvesting method on the post-thaw viability of the cells is shown in FIG. 17. The post thaw viability of the cells was high using both harvest methods.

Cells harvested by each of the methods (agitation or vibration) were cryopreserved. The cells were thawed, seeded with concentration of 10,000 cells/ml/well in a 24 well plate. The plates were incubated in a humidified incubator at 37° C. and 5% $CO_2$ for 1 or 4 days. The post-thaw vitality of the cells was assessed based on the MTT assay O.D. Each sample was tested in triplicate.

Figure 18:
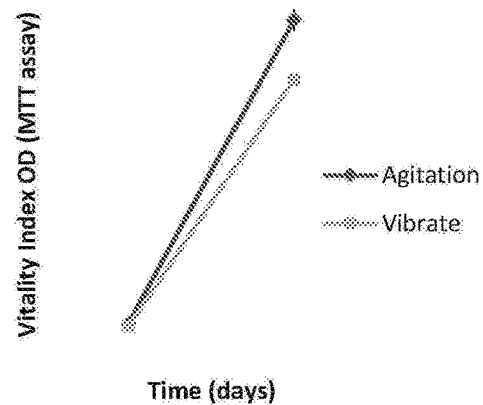
FIG. 18 shows the post-thaw vitality index for cells that were harvested by agitation or vibration.

The effect of the harvesting method on the post-thaw vitality of the cells is shown in FIG. 18. It can be seen that no difference in the post-thaw vitality of the cells, harvested using both methods, was found on day one, whereas the post-thaw vitality of the cells harvested using the vibration system was slightly lower at day 4 compared to the cells harvested applying the agitation method.

Example 5

We used a dye method to evaluate the circulation and mixing time of fluid within the vibrating 3D matrix packed bed. The circulation efficacy imparted by the vibration was assessed according to the measurements of the two following parameters:

Circulation time: The time period between initiation of vibration until the red dye introduced into center of the packed bed is observed outside of the packed bed.

Mixing time: The time period between initiation of vibration until the red dye is uniformly distributed throughout the bioreactor vessel.

Procedure:

The vibration harvest system bioreactor embodiment developed by Pluristem in cooperation the ARAN Research & Development (see FIGS. 6 and 9A-D) was filled with 3.6 L of double distilled water. One ml of Duracet Luminous red dye was injected using an injection device into the middle of the basket at two different sites, 0.5 ml of dye at each site.

Circulation and mixing times were measured while vibrating the basket at an amplitude of 25 mm using frequencies of 1, 2, or 3 Hz. The results are presented in the following table:

| Frequency (Hz) | Circulation Time (Sec) | Mixing Time (Sec) |
| --- | --- | --- |
| 1 | 8 | 70 |
| 2 | 4 | 55 |
| 3 | 3.5 | 30 |

The packed bed circulation time and mixing time that were measured by visual inspection of the dye indicate that the vibration motion will generate circulation of liquid inside and outside the basket of the bioreactor. The Packed bed circulation time and mixing times are sufficient to have uniform flow inside the basket and in the vessel to enable seeding and growing cells uniformly without using an impeller to generate cell suspensions and circulate medium.

Example 6

In this experiment, a 5 L harvest system was tested for cell growth and harvest efficiency. The harvest parameters that were evaluated were: the vibration frequency and the vibration duration (using an amplitude of 25 mm). During the entire harvest process biomass was monitored on-line and the cell suspension was sampled for cell counts at certain points.

Capacitance values, which correlate with the number of viable cells, were measured in order to monitor harvest performance using a biomass monitor from Aber Instruments.

Figure 19:
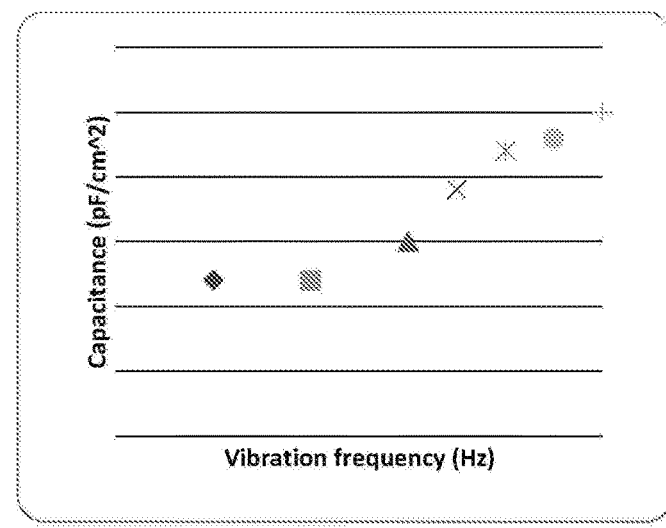
FIG. 19 demonstrates a positive correlation between vibration frequency and harvest efficiency as measured by capacitance values. The highest harvest efficiency was obtained using a frequency of 5 Hz.

The capacitance values as a function of vibration frequency are shown in FIG. 19. As seen in the Figure, a correlation was demonstrated between the vibration frequency and harvest efficiency, as measured by capacitance values of the suspension. The highest harvest efficiency was obtained at frequency of 5 Hz, which is the technical maximum frequency of the system.

The number of cells attached to the FibraCel disk-carriers was assessed, before and after harvest, using the MTT assay as previously described. Harvest efficiency was calculated according to the following formula:

$$\frac{OD \text{ value before harvest} - OD \text{ value after harvest}}{OD \text{ value before harvest}} \times 100$$

The value represents the percentage of cells removed from the carriers after harvest (a high value=a high harvest efficiency, and vice versa). Carriers were sampled after harvest from different depths in the basket in order to evaluate harvest efficiency and uniformity. The carrier MTT assay results (O.D) and harvest efficiency (%) in different depths of the basket are presented in the next table:

| | Before Harvest | After Harvest Top | After Harvest Middle | After Harvest Bottom |
| --- | --- | --- | --- | --- |
| Average O.D | 0.557 | 0.048 | 0.080 | 0.096 |
| STD | 0.161 | 0.010 | 0.030 | 0.079 |
| Harvest efficiency (%) | NA | 97.6 | 91.5 | 88.4 |

Figure 20:
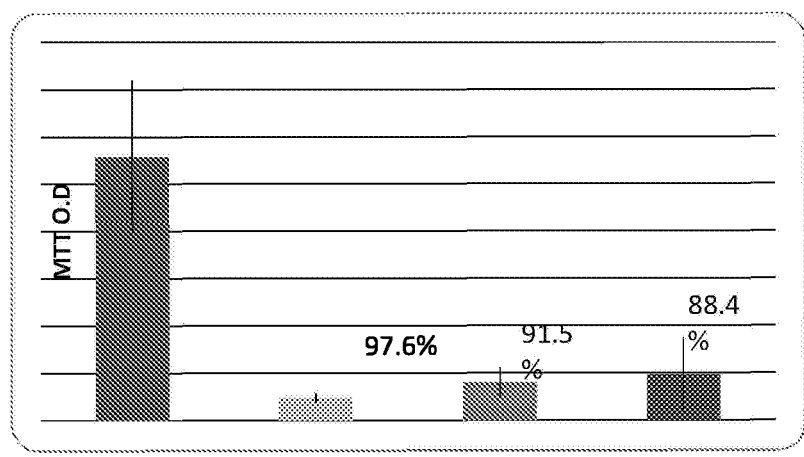
FIG. 20 shows the harvest efficiency for cells harvested by vibration with sampling of carriers taken from different positions within the basket holding the carriers.

The harvest efficiencies at the top, middle and bottom of the basket were 97.6%, 91.5% and 88.4%, respectively (see FIG. 20). This indicates that the use of vibration provides an effective and uniform harvest procedure in the entire basket under the specified harvest conditions.

Carriers MTT assay results (O.D) and harvest efficiencies for the designed (harvest by vibration) and original (harvest by agitation) baskets were compared in order to evaluate harvest performance. The "original" basket is an off-the-shelf product that includes two horizontally positioned, perforated metal screens that extend to the inner walls of the bioreactor vessel (as shown in FIG. 4A). Enclosed between those screens a bed of Fibracel® disks serves as a solid support matrix for cell growth. The "designed" basket developed by Pluristem is an improvement on the original basket in that due to the basket's dimensions it is not in contact with the interior wall of the glass vessel, facilitating its reciprocating movement. Also, as shown in FIG. 6, the designed basket includes a basket seal that prevents media from flowing between the bioreactor vessel and the basket walls.

The results are shown in the following table:

|  | Designed Before Harvest | Designed After Harvest* | Original Before Harvest | Original After Harvest |
|---|---|---|---|---|
| Average O.D | 0.557 | 0.075 | 0.568 | 0.101 |
| STD | 0.161 | 0.052 | 0.108 | 0.022 |
| Harvest efficiency (%) | 92.5 | | 88.9 | |

Figure 21:
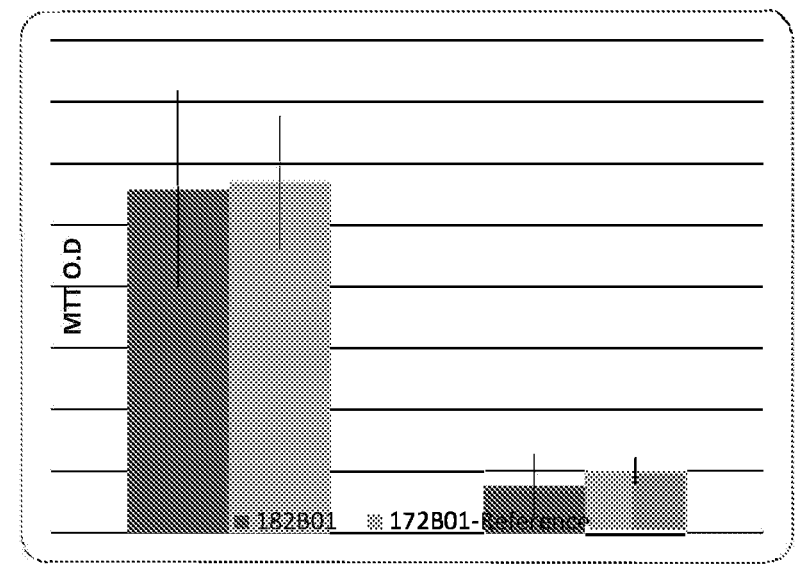
FIG. 21 shows the harvest efficiency obtained for cells harvested by vibration using two different baskets for the 3D carriers.

*Data present average values of carriers sampled from different depths of the basket Overall agitation harvest efficiencies were 92.5% for the designed basket compared to 88.9% for the original basket (see FIG. 21).

In another experiment, an amplitude of 25 mm and frequency of 5 Hz were used to test the effect of vibration duration on harvest efficiency and cell quality. The effect of incubation time before applying the vibration force was examined by applying gentle vibration using an amplitude of 25 mm and frequency of 1 Hz to enable efficient mixing of the solutions (DPBS and TrypLE).

During the entire harvest process on-line biomass monitoring was applied and cell suspensions were sampled for cell counts at certain points. The result are presented in the following table:

| Harvest Step | Capacitance (pF/cm$^2$) | Cell concentration (Cells × 10$^6$/ml) | Viability (%) |
|---|---|---|---|
| First wash (DPBS) | 0.7 | NP | NP |
| Second wash (DPBS) | 0.0 | NP | NP |
| Pre- incubation (TrypLE) | 1.0 | 0.131 | 95 |
| Incubation of 8 min (TrypLE) | 1.5 | 0.208 | 84.3 |
| Vibration of 30 seconds (5 Hz) | 3.7 | 0.775 | 95 |
| Vibration of 60 seconds (5 Hz) | 5.1 | 0.825 | 92.5 |
| Vibration of 90 seconds (5 Hz) | 5.5 | 0.75 | 89.5 |
| Vibration of 120 seconds (5 Hz) | 5.6 | 0.766 | 91.6 |
| Wash with DPBS | 1.6 | 0.238 | 88 |
| Second TrypLE treatment | 0.6 | NP | NP |

Figure 22:
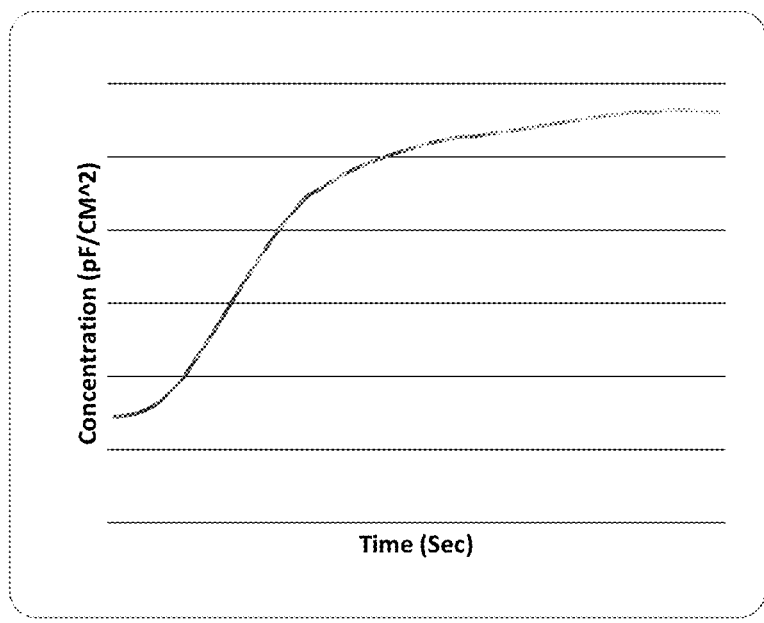
FIG. 22 shows cell concentrations (measured as capacitance values) as a function of vibration duration for cells harvested by vibration using a frequency of 5 Hz.

Capacitance values as a function of vibration duration at a frequency of 5 Hz are shown in FIG. 22.

Figure 23:
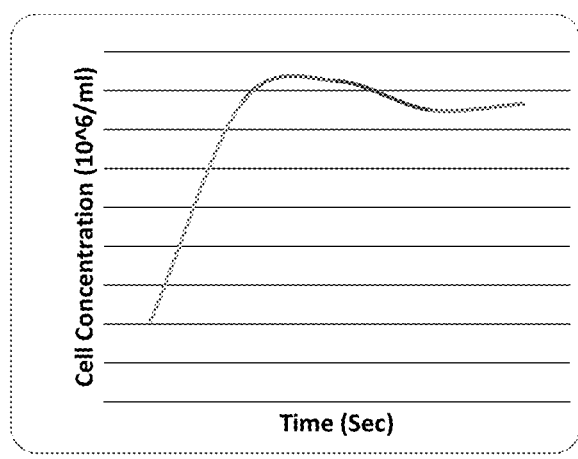
FIG. 23 shows cell concentrations as a function of vibration duration for cells harvested by vibration using a frequency of 5 Hz.

Cell concentration and viability were determined using the Countess at the end of each step. Cell concentrations as a function of vibration duration at a frequency of 5 Hz are presented in FIG. 23.

The harvest process (at a frequency of 5 Hz) was very effective within the first 30 seconds, as measured by cell concentration, and within the first 60 seconds as measured by the capacitance values of the suspension. Continuing the vibration for additional time did not have much effect on cell yields according to both cell concentration and capacitance values.

In addition, extending the vibration duration up to 120 seconds did not have a significant impact on cell viability, which was above 84% in all cases.

Carrier MTT assay results (O.D) and harvest efficiencies (%) in different depths of the basket are presented in the next table:

|  | Before Harvest | After Harvest Top | After Harvest Middle | After Harvest Bottom | After Harvest AVG* |
|---|---|---|---|---|---|
| Average O.D | 1.059 | 0.081 | 0.206 | 0.064 | 0.117 |
| STD | 0.266 | 0.057 | 0.147 | 0.065 | 0.115 |
| Harvest efficiency (%) | NA | 92.4 | 80.6 | 94.0 | 89.0 |

Figure 24:
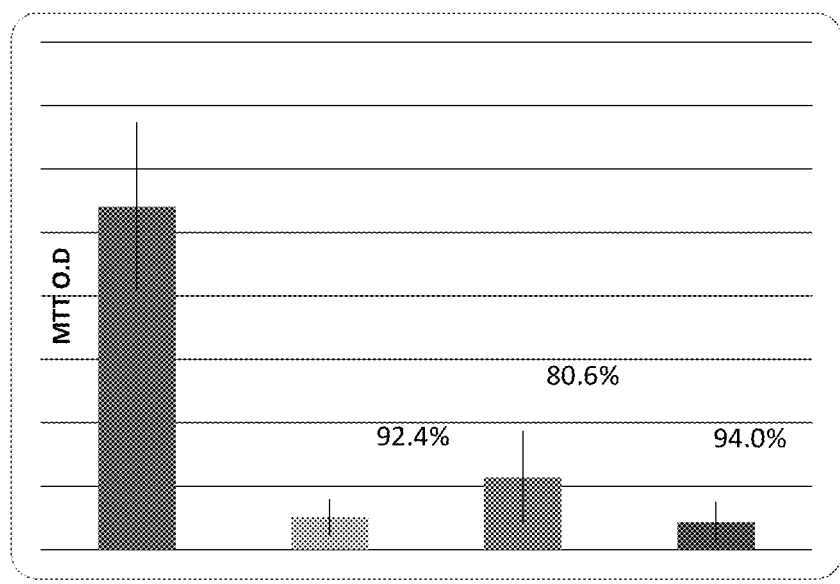
FIG. 24 shows the harvest efficiency for cells harvested by vibration with sampling of carriers taken from different positions within the basket holding the carriers.

*Data present average values of carriers sampled from different depths of the basket The harvest efficiency at the top, middle and bottom of the basket were 92.4%, 80.6% and 94.0%, respectively (see FIG. 24), which indicates an effective harvest procedure (>80%) in the entire basket under the specified harvest conditions. The overall harvest efficiency was 89%, which is higher than the efficiency of the currently-used agitation harvest method.

Cells were also seeded at a concentration of 30,000 cells/ml/well in a 24 well plate for vitality testing. The plates were incubated in humidified incubator at 37° C. and 5% $CO_2$ for 24 hours. The vitality test was based on the MTT assay, with each sample tested in triplicate.

The effect of vibration duration on the vitality of (fresh) cells is presented in the next table:

|  | Pre-Incubation | 0 sec | 30 sec | 60 sec | 90 sec | 120 sec |
|---|---|---|---|---|---|---|
| AVG MTT O.D | 0.147 | 0.195 | 0.216 | 0.192 | 0.206 | 0.181 |
| STD | 0.016 | 0.014 | 0.003 | 0.009 | 0.008 | 0.013 |

Figure 25:
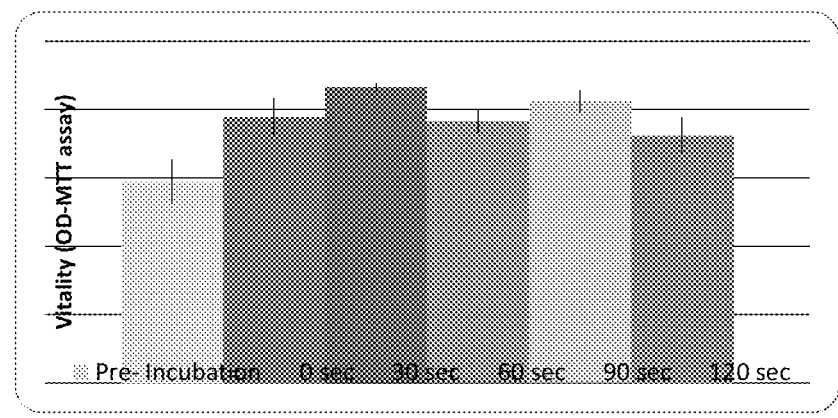
FIG. 25 shows a vitality index for cells harvested by vibration with a vibration duration lasting up to 120 second.

The data are also shown in FIG. 25. The vitality test results demonstrate no significant effect of the vibration duration (up to 120 seconds) on cells vitality. These results demonstrate the efficiency of the ability of the vibrations harvest system in terms of cell yield, harvest uniformity, and cell quality.

Example 6

This experiment demonstrates the effectiveness of the vibration harvest method in recovering cells grown on different 3D matrices.

To test the utility of the vibration-based harvest method with different types of 3D matrices, human placenta-derived ASCs were seeded onto three types of adherent 3D matrices: a porous gelatin sponge, a 34 μm woven fiber matrix, and a 70 μm woven fiber matrix. After seeding and a period of cell growth (3 or 5 days), cells were harvested from the matrices by vibration. The MTT assay, cell staining, and cell counts were used to determine harvest efficiency.

The 3D porous gelatin sponge used in this example was the Spongostan® sponge (Ethicon, N.J.). The sponge was cut into 3 cm×1 cm pieces in a biological hood. Ten pieces of the sponge were hydrated in 45 ml of Dulbecco's Minimal Essential Medium ("DMEM") supplemented with 2 mM L-glutamine, 10% FBS, and 50 mg/ml Gemtamicine ("complete DMEM") in a 50 ml vessel (two vessels total) overnight.

The hydrated sponge was placed into a six-well plate, with excess fluid having been removed from the sponges. To seed the sponges, 1×10$^7$ ASCs were thawed and the cell concentration was adjusted to 2×10$^6$ cells/ml. Each sponge was seeded with 100 μl of cell suspension (200,000 cells). The sponges were placed in an incubator (37° C., 5% $CO_2$) for 45 minutes, and the cell suspension was held on ice. After the 45 minutes, the sponges were turned upside-down and an additional 100 µl (200,000 cells) was seeded on each sponge. This was followed by another 45 minute incubation. After this second incubation, two sponges each were placed into 50 ml tubes (5 tubes total) with 20 ml of complete DMEM. The caps on the tubes were left slightly open for gas exchange and the tubes were incubated (37° C., 5% $CO_2$) for five days to permit cell growth.

The 34 µm woven fiber matrix (PETEX; Polyester precision woven screens, fiber diameter 34 µm, SEFAR, Switzerland) and the 70 µm woven fiber matrix (PES; Polyester, fiber diameter 70 µm, SAATI, Italy) were each cut into 1×0.5 cm pieces. The cut pieces of the matrix were dispensed into a spinner flask basket and autoclaved. Afterward, 150 ml of complete DMEM was added to each spinner flask and the matrices were hydrated overnight.

To seed the PETEX and PES fiber matrices, the DMEM was replaced with 150 ml of fresh complete DMEM. To each spinner flask 1.4×107 ASCs were added and the spinner flasks were placed in an incubator (37° C., 5% $CO_2$) for four hours with the spinners rotating at a rate of 40 RPM. After four hours, the rotation rate was raised to 120 RPM and the ASCs were permitted to grow for five days.

ASCs grown on the carriers were harvested by vibration as follows. The spinner flasks and the 50 ml tubes were removed from the incubator. Ten woven carriers of each size (34 µm and 70 µm) were used for cell staining and assessment using the MTT assay. Similarly, two sponge carriers (each sponge cut into three pieces) were used for cell staining and the MTT assay.

The culture media was discarded and the gel sponges were washed twice with PBS. The sponges were cut in half and placed into a spinner flask packed bed and the packed bed was placed into a container filled with 800 ml of pre-warmed (37° C.) TrypLE. The sponges were then immediately vibrated for 5 seconds at 5 Hz, 5 minutes at 1 Hz, and 30 seconds at 5 Hz (all with an amplitude of 25 mm). Following the vibration, 200 ml of FBS was added and the medium was transferred to two 500 ml centrifuge tubes. The cells were centrifuged at 1,200 RPM for 10 minutes at 4° C., the cell pellet was resuspended, and cell counts were performed. The two types of woven carriers were processed in a similar fashion, and cells were harvested from those carriers using the same vibration conditions.

In addition, the matrices were stained before and after cell harvest with Hoechst 33258 nuclear stain and cells were visualized by fluorescent microscopy. By this direct visualization (results not shown), the vibrations harvest method shown to efficiently remove most viable cells from the different types of 3D matrices tested. These results were confirmed by the MTT assay O.D. values.

MTT Results

| | Avg. OD reading (background subtracted) | Standard Deviation | Percent of cell removal |
| --- | --- | --- | --- |
| Woven 70 micron BV | 0.152375 | 0.032754 | |
| Woven 70 micron AV | 0.012875 | 0.013569 | 91% |
| Woven 35 micron BV | 0.08725 | 0.025949 | |
| Woven 35 micron AV | 0.00125 | 0.004062 | 98% |
| Gelatin sponge BV | 0.305 | 0.088019 | |
| Gelatin sponge AV | 0.091625 | 0.018419 | 69% |

BV—before vibration
AV—after vibration

Vibration of 3D matrices resulted in high percentages of cell removal, above 90% for the woven 3D matrices, and 69% for the porous gelatin sponge. In this experiment, no attempt was made to optimize the vibration characteristics for maximizing cell recovery from these specific matrices, so it may be possible to obtain even higher cell recovery efficiencies.

Cell counting and viability results are presented in the following table:

Cell Counting and Viability Results

| | Cells removed | Viability (Trypan Blue) |
| --- | --- | --- |
| Woven 70 micron | 2.18E+07 | 87% |
| Woven 35 micron | 1.70E+07 | 85% |
| Gelatin sponge | 6.20E+06 | 88% |

Based on these data, the vibration-based cell harvest method is effective in removing cells from each of the tested 3D matrices while maintaining a high degree of cell viability.

These results demonstrate that the vibration cell harvest method is highly effective with a wide range of 3D scaffold types.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are incorporated in their entirety by reference into the specification, to the same extent as if each individual publication, patent or patent application was specifically and individually indicated to be incorporated herein by reference. In the event the material incorporated by reference conflicts with the disclosure in the specification, the specification herein prevails. In addition, citation or identification of any reference in this application shall not be construed as an admission that such reference is available as prior art to the present invention.

We claim:

1. A method of seeding cells in a 3-dimensional matrix in a chamber of a bioreactor, comprising:
   a) providing a three-dimensional matrix in a fluid within a container, which container is disposed within said chamber;
   b) introducing a composition comprising cells into the container;
   c) vibrating the container in a reciprocating motion relative to said chamber for a period of time at a frequency and amplitude sufficient to mix the cells throughout the matrix; and
   d) discontinuing the vibration to permit the cells to attach to the matrix.

2. The method of claim 1, wherein the fluid is a growth medium.

3. The method of claim 2, further comprising growing the cells in the bioreactor by applying intermittent vibration to the container for a period of time at a frequency and amplitude sufficient to mix the growth medium throughout the matrix.

4. The method of claim 1, wherein the 3-dimensional matrix is enclosed in a packed bed within said container.

5. The method of claim 4, wherein the 3-dimensional matrix comprises a single-piece scaffold, multiple beads, multiple carriers, microfibers, nanofibers, or combinations thereof.

6. The method of claim 5, wherein the microfibers or nanofibers are woven or non-woven.

7. The method of claim 5, wherein the beads are porous.

8. The method of claim 1, wherein the 3-dimensional matrix comprises an adherent material.

9. The method of claim 8, where the adherent material comprises one or more of a polyester, a polypropylene, a polyalkylene, a polyfluorochloroethylene, a polyvinyl chloride, a polyvinyl fluoride resin, a polystyrene, a polysulfone, a polyurethane, a polyethyene terephtalate, a cellulose, a glass fiber, a ceramic particle, a matrigel, an extracellular matrix component, a collagen, a poly L lactic acid, a dextran, an inert metal fiber, silica, natron glass, borosilicate glass, chitosan, or a vegetable sponge.

10. The method of claim 8, wherein the adherent material is electrostatically charged.

11. The method of claim 1, wherein the cells are human cells.

12. The method of claim 11, wherein the human cells are adherent cells.

13. The method of claim 12, wherein the adherent cells are adherent stromal cells.

14. The method of claim 13, wherein the origin of the adherent stromal cells is placenta, adipose tissue, or bone marrow.

15. The method of claim 14, wherein the origin of the adherent stromal cells is placenta.

16. The method of claim 15, wherein the adherent stromal cells are obtained from a fetal part of the placenta.

17. The method of claim 15, wherein the adherent stromal cells are obtained from a maternal part of the placenta.

18. The method of claim 1, wherein the container is vibrated by a substantially linear reciprocating motion.

19. The method of claim 18, wherein the reciprocating motion has an amplitude of between about 10 mm to about 750 mm and a frequency of 1 to 3 Hz.

20. The method of claim 18, wherein the amplitude of the substantially linear reciprocating motion is a distance that is 15-100% of the height of said container.

* * * * *